(12) United States Patent
Yanuma et al.

(10) Patent No.: US 8,372,029 B2
(45) Date of Patent: Feb. 12, 2013

(54) FLUID FEEDER, BALLOON CATHETER AND FLUID FEEDER SUPPORTING DEVICE

(75) Inventors: Yutaka Yanuma, Tokyo (JP); Saki Yamaguchi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/475,054

(22) Filed: May 29, 2009

(65) Prior Publication Data

US 2009/0259211 A1 Oct. 15, 2009

Related U.S. Application Data

(63) Continuation-in-part of application No. 12/046,744, filed on Mar. 12, 2008, now abandoned.

(51) Int. Cl.
*A61N 1/30* (2006.01)

(52) U.S. Cl. ......................................................... 604/19

(58) Field of Classification Search ............... 604/97.01, 604/97.02, 97.03, 99.01, 186, 207, 210, 19; 222/43
See application file for complete search history.

(56) References Cited

U.S. PATENT DOCUMENTS

| | | | |
|---|---|---|---|
| 5,634,910 A | 6/1997 | Kanner et al. | |
| 5,752,935 A | 5/1998 | Robinson et al. | |
| 6,063,057 A | 5/2000 | Choh | |
| 6,234,996 B1 | 5/2001 | Bagaoisan et al. | |
| 6,267,717 B1 | 7/2001 | Stoll et al. | |
| 2004/0019323 A1 | 1/2004 | Carter et al. | |
| 2004/0260237 A1 | 12/2004 | Squadrito | |
| 2005/0015048 A1 | 1/2005 | Chiu et al. | |
| 2007/0142818 A1 | 6/2007 | Webler et al. | |

FOREIGN PATENT DOCUMENTS

JP 2008-049199 3/2008

OTHER PUBLICATIONS

Extended Partial European Search Report dated Sep. 30, 2009.
European Office Action dated Aug. 27, 2012 in related European Patent Application No. 09003549.4.

*Primary Examiner* — Nicholas Lucchesi
*Assistant Examiner* — Brooke Matney
(74) *Attorney, Agent, or Firm* — Scully, Scott, Murphy & Presser, P.C.

(57) ABSTRACT

A fluid feeder (1, 31) which feeds a fluid into a balloon (4) made of an elastic material so as to inflate, the fluid feeder provided with: a cylinder (12) that is formed in a cylindrical shape provided with a first end (12A) and a second port (12B) on each end thereof and contains the fluid; a plunger (13) that is inserted into the cylinder via the second end in a freely advancing and retracting manner in an axial direction, in order to push out the fluid contained in the cylinder from the first end to the outside of the cylinder; an adjustor (14, 32) that is attached to the plunger and regulates a moving distance of the plunger so as to inflate the balloon to a predetermined diameter; and a fixing portion (15) that is provided on the cylinder and fixes the plunger onto the cylinder to a position which corresponds to the moving distance regulated by the adjustor, wherein:
the adjustor has a plurality of engaging projections (18, 33) which regulates the moving distance corresponding to a plurality of the different inflated diameters, and the fixing portion has an engaged portion (19) which engages with the engaging projections to fix the plunger.

32 Claims, 24 Drawing Sheets

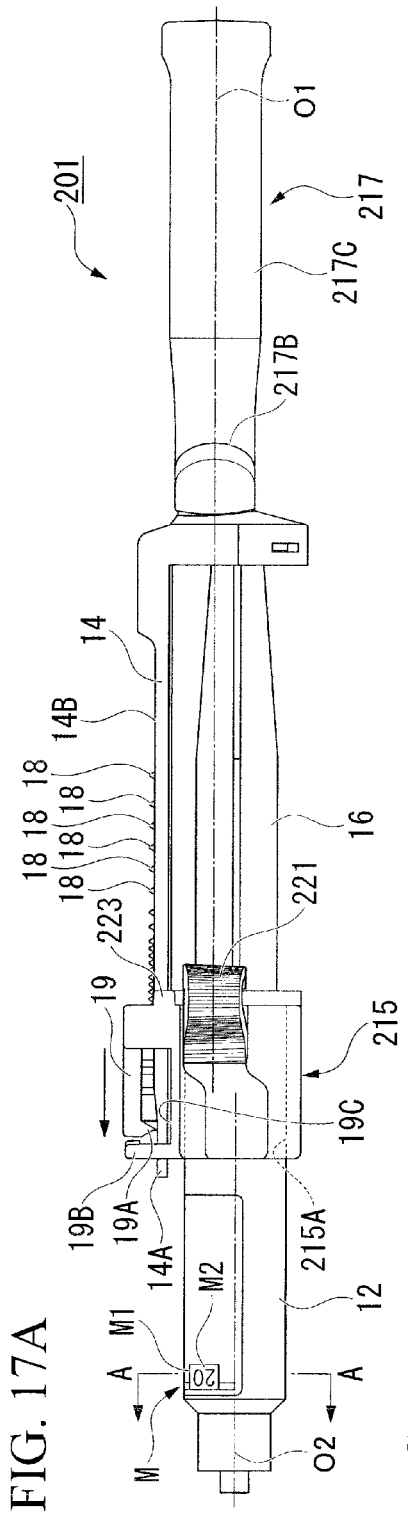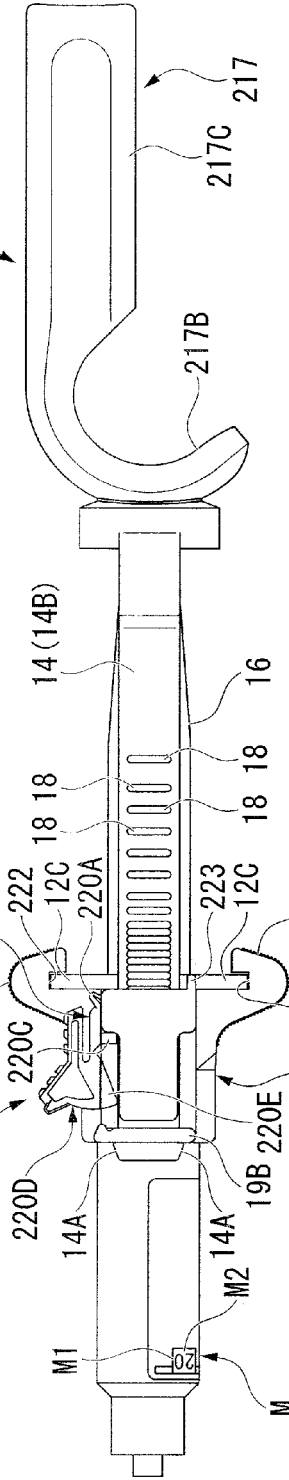

FLUID FEEDER, BALLOON CATHETER AND FLUID FEEDER SUPPORTING DEVICE

BACKGROUND OF THE INVENTION

1. Field of the Invention

The present invention relates to a fluid feeder, a balloon catheter and a fluid feeder supporting device which are employed by feeding fluid into a balloon.

Priority is claimed on U.S. patent application Ser. No. 12/046,744, filed on Mar. 12, 2008, the content of which is incorporated herein by reference.

2. Description of Related Art

In general, various types of balloon catheters provided with a balloon in the vicinity of a distal end of the catheters are employed in a medical field, for example, urological catheters provided with a balloon for medical use such as indwelled urinary catheters, endotracheal tubes, digestive tract catheters and cardiac balloon catheters for cardiac pumping (for example, U.S. Pat. No. 6,267,717, U.S. Pat. No. 6,063,057, U.S. Patent Application Publication No. 2004/19323).

When the balloon of the balloon catheters is inflated, in general, a fluid feeder (such as a syringe of medical use) is fitted onto a port located at a handheld side which is connected to the balloon so as to flow a fluid. The balloon is inflated to a required volume by injecting the fluid.

When a gallstone is removed with the balloon catheters described above, a balloon 100 is inflated with a slightly larger diameter than that of a bile duct 110. Thereafter, a gallstone 111 is carried closer to the entry of the bile duct by scraping the gallstone 111 with the balloon 100.

Due to the narrow diameter of the entry of the bile duct, the balloon catheters carrying the gallstone can not be withdrawn from the bile duct without reducing the diameter of the balloon 100. Therefore, in normal practice, an assistant operates the fluid feeder in conjunction with the balloon 100 being pulled by a user; hence the pulling operation is performed by deflating the balloon 100.

However, it is not easy to synchronize the operations of the user and the assistant. If the synchronized operation is not carried out correctly; in this case, if the deflation of the balloon 100 is too fast, the gallstones 111 is separated from the balloon 100 and left in the bile duct.

On the other hand, if the deflation of the balloon 100 is too slow, the balloon 100 may compress the exit of the bile duct 110, or the balloon 100 may rupture.

Further, as the diameter of the balloon becomes smaller and smaller, the diameter will change significantly with a slight operation of the fluid feeder. This is problematic as adjustment of the diameter of the balloon to a desirable size becomes difficult as a result.

In most cases, when a gall stone is removed by using a balloon catheter, various operations including retracting and advancing movements of the balloon catheter, inflation and deflation of the balloon, manipulation of a guidewire and a syringe used for injecting a contrast agent and the like, are required so as to be performed simultaneously; making the user's handheld manipulation at his or her side cumbersome and complicated. Therefore, it is difficult to conduct an entire operation by the user. In addition, even if an assistant assists the operation, burden to the assistant (due to the cumbersome and complicated operation) is large. Furthermore, once the assistant is involved with an operation, it is necessary to synchronize the operation of the user and the assistant.

Furthermore, in a conventional balloon inflation and deflation operation, a diameter of the balloon was maintained to a certain diameter by placing a stopcock between a syringe used for general medical use and a connector provided on a handheld side of the catheter, then a tube connected to the syringe and a tube connected to the catheter are separated by switching the stopcock. In order to adjust the diameter of the balloon at a specific size, a simultaneous manipulation of the stopcock was required while manipulating the syringe for general medical use, and both of the user's hands were required for these manipulations. Hence, the inflation and deflation operation of the balloon was difficult to perform simultaneously so that the entire operation of gallstone removal was cumbersome and complicated.

SUMMARY OF THE INVENTION

The present invention was conceived in view of the above-described circumstances, and has as its objective the provision of a fluid feeder which can adjust/control the diameter of a balloon to a desirable diameter regardless of the diameter of the balloon.

Another object of the present invention is the provision of a balloon catheter which can reliably adjust the diameter of the balloon to a desirable diameter.

Another object of the present invention is to provide of a fluid feeder and a supporting device thereof which can adjust/control the diameter of the balloon to a desirable diameter during a balloon inflation and deflation manipulation.

According to a first aspect of the present invention, a fluid feeder which feeds a fluid into a balloon made of an elastic material so as to inflate, the fluid feeder provided with: a cylinder that is formed in a cylindrical shape provided with a first port and a second port on each end thereof, and contains the fluid; a plunger that is inserted into the cylinder via the second port in a freely advancing and retracting manner in an axial direction, in order to push out the fluid contained in the cylinder from the first port to the outside of the cylinder; an adjustor that is attached to the plunger and regulates a moving distance of the plunger so as to inflate the balloon to a predetermined diameter; and a fixing portion that is provided on the cylinder, and fixes the plunger onto the cylinder to a position which corresponds to the moving distance regulated by the adjustor; wherein:

the adjustor has a plurality of engaging members which regulates the moving distance corresponding to a plurality of the different inflated diameters, and the fixing portion has an engaged portion which engages with the engaging members to fix the plunger.

According to a second aspect of the present invention, a balloon catheter provided with a balloon made of an elastic material, and includes the fluid feeder of the present invention.

According to a third aspect of the present invention, a fluid feeder supporting device is provided to be attached onto the cylinder and the main body of the plunger, that is used for inflating a balloon made of an elastic material by feeding a fluid thereinto. The fluid feeder supporting device is provided with:

an adjustor that is detachably attached to the main body of the plunger and regulates a moving distance of the main body of the plunger so as to inflate the balloon to a predetermined diameter;

and a fixing portion that is detachably attached to the cylinder, and fixes the plunger onto the cylinder with a position which corresponds to the moving distance regulated by the adjustor; wherein:

the adjustor has a plurality of engaging members which regulates the moving distance corresponding to a plurality of the different inflated diameters, and the fixing portion has an engaged portion which engages with the engaging members so as to fix the main body of the plunger.

According to a fluid feeder and a fluid feeder supporting device of the present invention, a diameter of the balloon can be adjusted/controlled to any desirable diameter, regardless of the diameter of the original balloon.

Furthermore, according to a balloon catheter of the present invention, a diameter of the balloon can be reliably adjusted/controlled to a desirable diameter.

BRIEF DESCRIPTION OF THE DRAWINGS

FIG. 17A shows a front view of the fluid feeder supporting device according to a third embodiment of the present invention.

FIG. 17B is a plain view of the fluid feeder supporting device of the present invention.

FIG. 17C is a cross-sectional view as seen from a line A-A of FIG. 17A.

DETAILED DESCRIPTION OF THE INVENTION

A fluid feeder according to a first embodiment of the present invention will be explained with reference to FIGS. 1 through 12.

Figure 1:
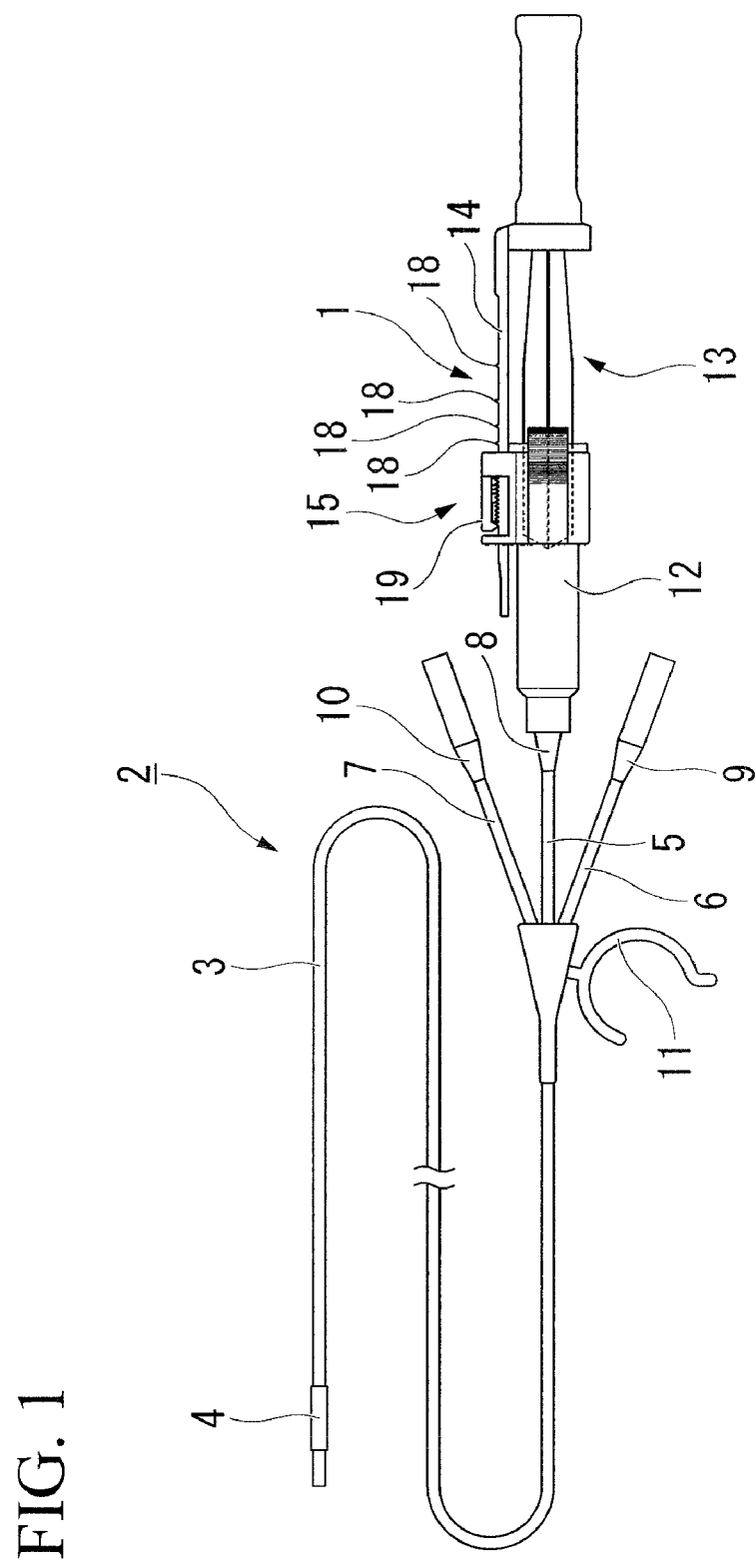
FIG. 1 shows the balloon catheter provided with the fluid feeder according to a first embodiment of the present invention.

FIG. 1 is a view showing a balloon catheter 2 provided with a fluid feeder 1 according to the present embodiment. The balloon catheter 2 includes a long flexible sheath 3, a balloon 4 provided in the vicinity of a distal end of the sheath 3, and the fluid feeder 1 provided at a proximal end of the sheath 3.

The sheath 3 is made of a flexible material, such as resin, and is provided with three lumens; a first lumen 5 for feeding fluid to a balloon 4, a second lumen 6 for inserting a guidewire which guides a distal end of the balloon catheter 2 to a desirable position of a body cavity of a patient, and a third lumen 7 for transporting various fluid, such as a contrast agent, into the body cavity of the patient.

A distal end of the first lumen 5 passes through an outer periphery surface of the sheath 3, and opens into the balloon 4. Distal ends of the second lumen 6 and the third lumen 7 open to the distal end of the sheath 3. However, the distal ends of the second lumen 6 and the third lumen 7 may also open at any position other than the distal end of the sheath 3.

The lumens 5, 6, 7 do not integrate each other, rather, they are provided within the sheath 3 independently. The three independent lumens extend and separate from the proximal ends, forming three ports: a first port 8, a second port 9 and a third port 10. The fluid feeder 1 is connected to the first port 8.

A proximal end of the sheath 3 also includes an anchor 11 which fixes the balloon catheter 2 at, for example, an endoscopic device or the like.

The balloon 4 is made of an elastic material so as to inflate by gradually expanding the diameter thereof when a fluid such as liquid or gas which is fed from the fluid feeder 1 accumulates inside thereof. As for the material made of the balloon 4, for example, natural rubber, synthetic rubber, polyurethane, polyamide elastomer, silicone, and the like can be employed suitably according to its purpose.

Figure 2:
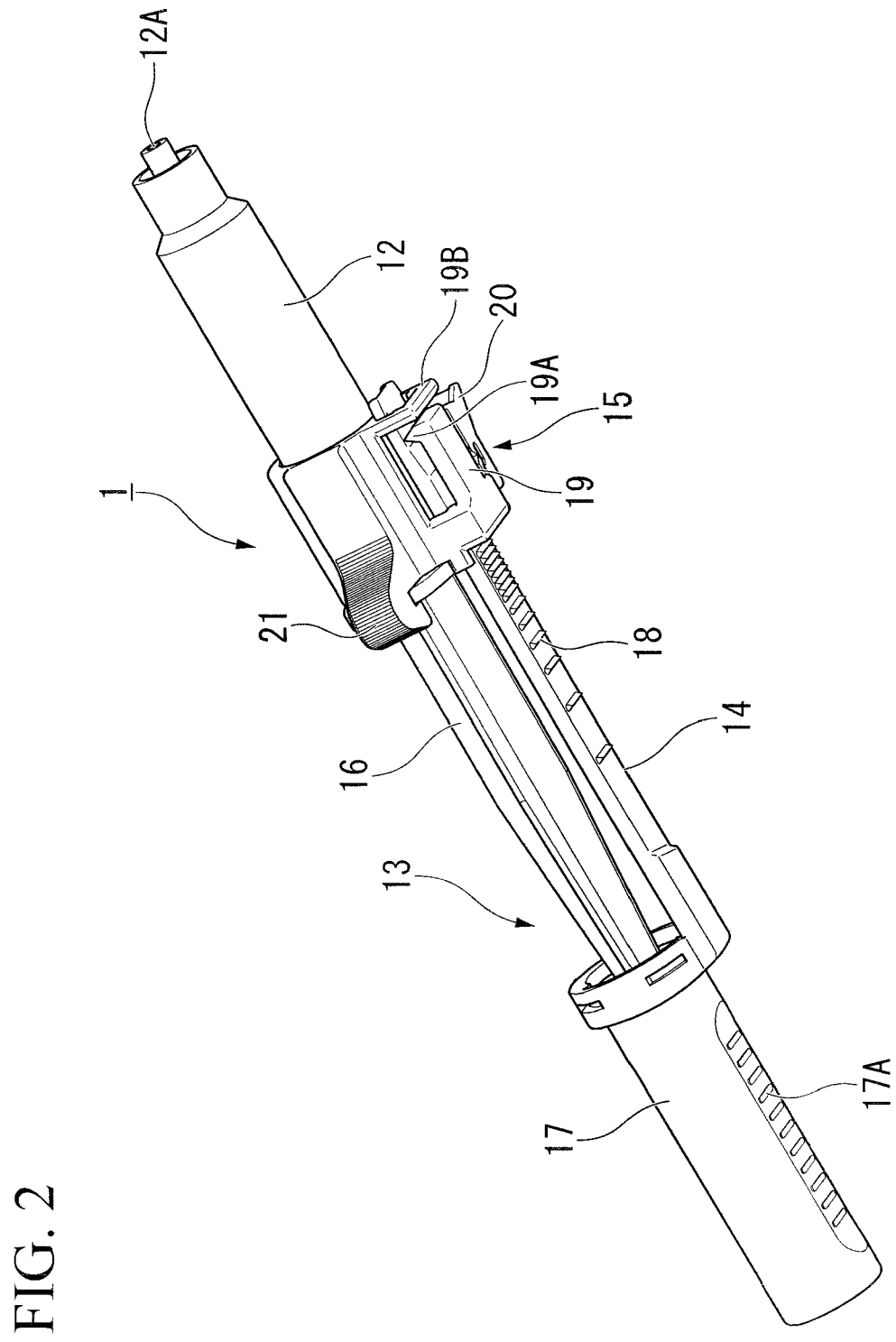
FIG. 2 is a perspective view of the fluid feeder of the present invention.
Figure 3:
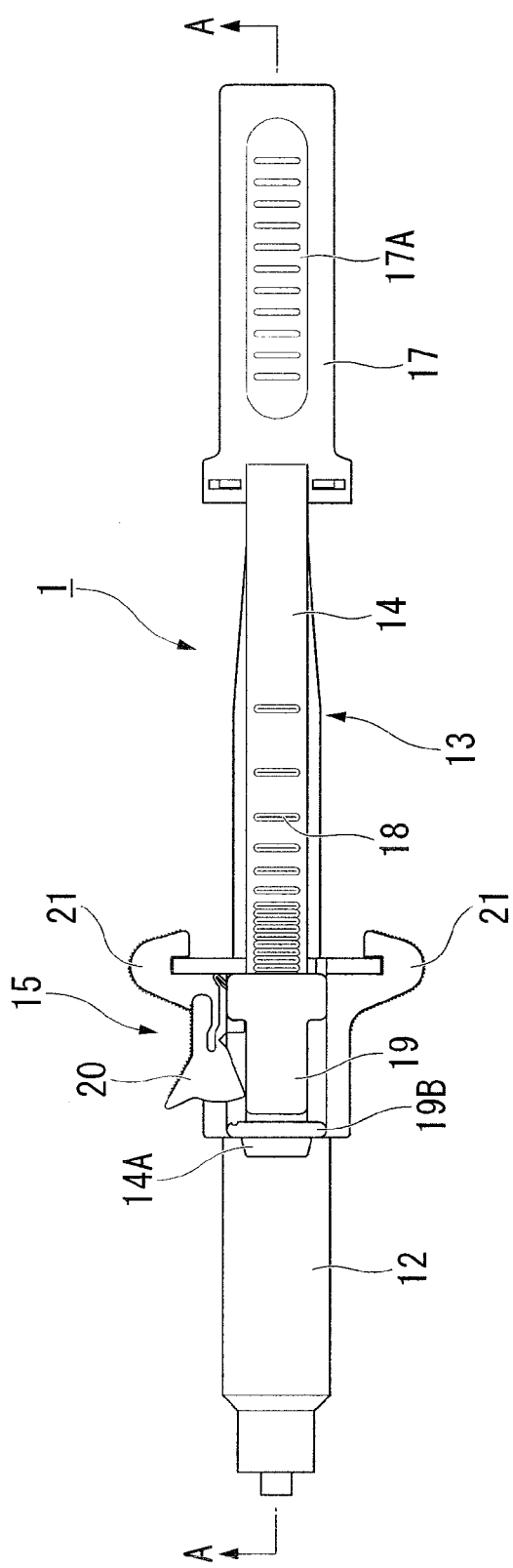
FIG. 3 is a plain view of the fluid feeder of the present invention.
Figure 4:
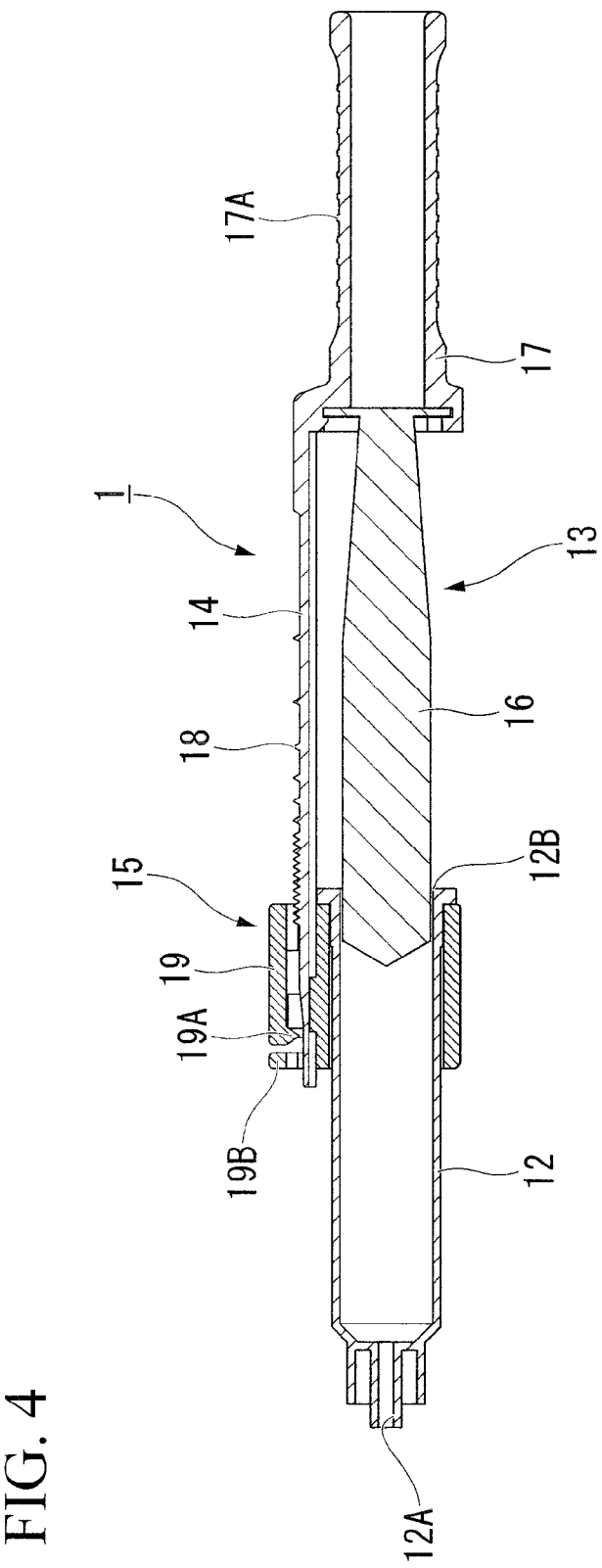
FIG. 4 is a cross-sectional view as seen from a line A-A of FIG. 3.

FIG. 2 is a perspective view of the fluid feeder 1, FIG. 3 is a plain view of the fluid feeder 1, and FIG. 4 is a cross-sectional view as seen from a line A-A of FIG. 3. As indicated in FIGS. 2 through 4, the fluid feeder 1 includes; a cylindrical-shaped cylinder 12, a plunger 13 which is inserted into the cylinder 12, an adjustor 14 provided on the plunger 13, and a fixing portion 15 provided on the cylinder 12.

The cylinder 12 is formed in a cylindrical shape, containing fluid inside a lumen thereof. The fluid contained may be a gas such as air, or a liquid, such as a saline solution. Both ends of the cylinder 12, a first end 12A at the distal end, and a second end 12B at the proximal end, are opened. The first end 12A engages with the first port 8 so that the shape of the first end 12A is constructed in a manner so as to allow engagement with the first port 8.

Figure 5:
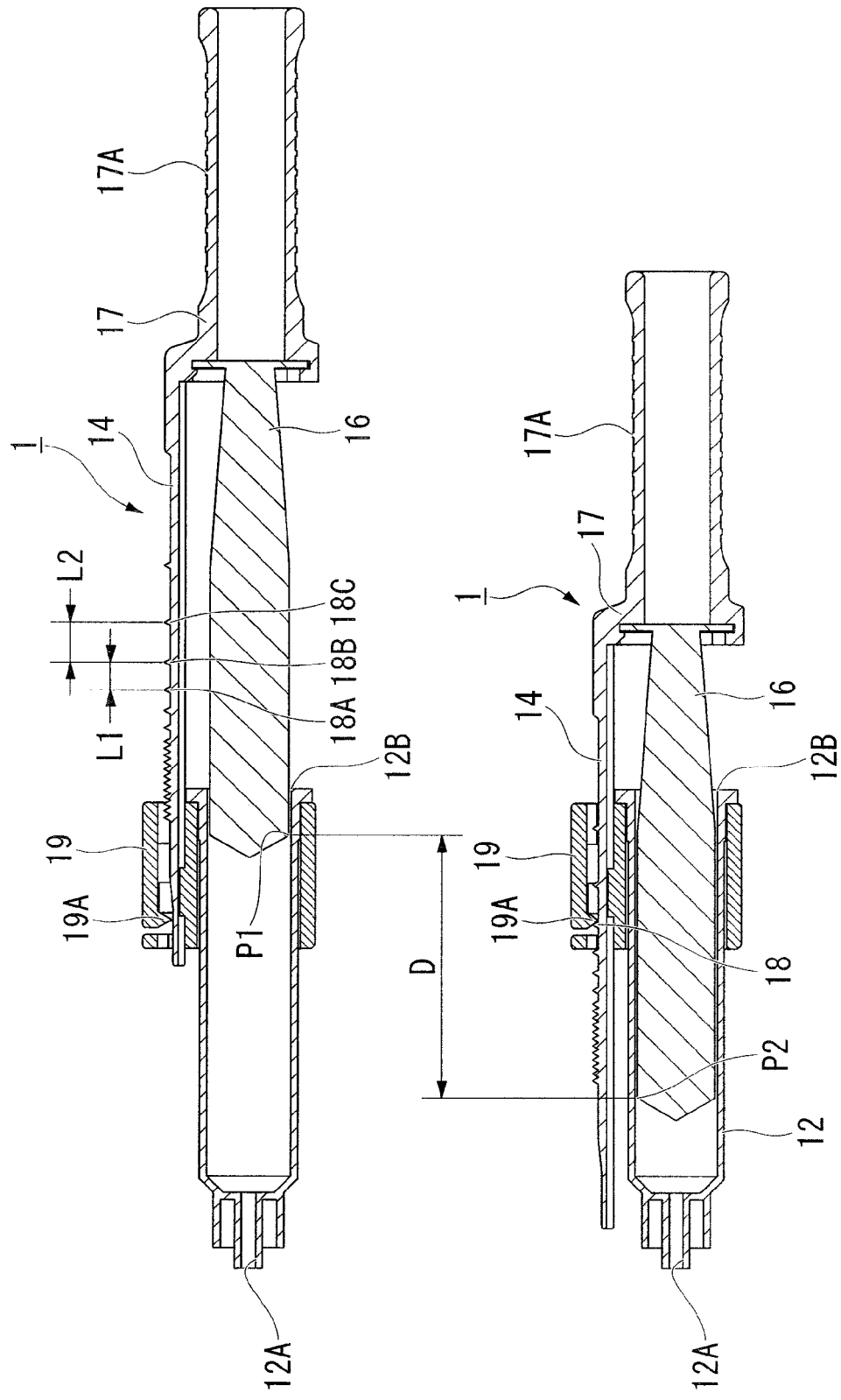
FIG. 5 shows an action of the plunger and the moving distance.

The plunger 13 includes a main body 16 which is inserted into the cylinder, and a grip 17 provided at a proximal side of the main body 16. A distal side of the main body 16 is inserted into the lumen of the cylinder 12, so as to advance and retract the main body 16 inside of the cylinder 12 along a longitudinal direction thereof. A shape of the distal end of the main body 16 is substantially the same as the inner diameter of the cylinder 12. As shown in FIG. 5, when the main body 16 is advanced toward the first end 12A of the cylinder 12, the fluid contained in the cylinder 12 is pushed out from the first end 12A.

A grip 17 is a member gripped by a user when the plunger 13 is operated, and there are no limits in the shape and material. The grip 17 in the proceeding embodiment is formed in a cylindrical-shape, provided with a slip resistance 17A for ease of gripping.

The adjustor 14 is a plate member extending from the grip 17 in a direction substantially parallel to the main body 16 of the plunger 13. A convex portion 14A (refer to FIG. 3) is formed at a distal end of the adjustor 14 so as to prevent the plunger 13 from escaping from the cylinder 12.

A plurality of engaging projections 18 which regulate an moving distance of the plunger 13 are formed on a surface of the adjustor 14 opposite to a surface facing to the main body 16. A distance between each of the engaging projections 18 is set longer as the position of the projections 18 is closer to the proximal end of the plunger 13. For example, as shown in FIG. 5, a distance L2 between an engaging projection 18B and an engaging projection 18C located more closer to the proximal side of the plunger 13 with respect to the projection 18B is longer than that of L1 between an engaging projection 18A and the engaging projection 18B located closer to the proximal side of the plunger 13 with respect to the projection 18A.

Figure 6:
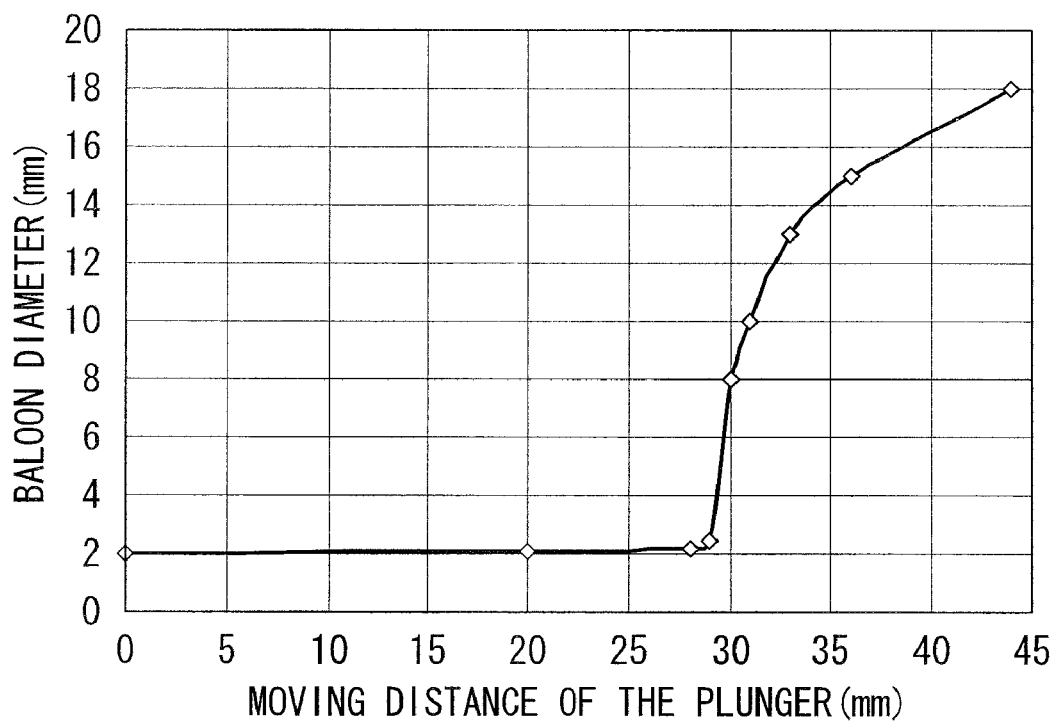
FIG. 6 is an example of a graph showing a relationship between the size of the diameter of the balloon and the moving distance of the plunger.

The distance between each of the engaging projections 18 is determined depending on the characteristics of the balloon 4 which are a target member for the fluid feeder 1 feeding a fluid thereinto. FIG. 6 shows an example of a graph indicating the relationship between the size of a diameter of the balloon and the moving distance of the plunger 13.

Note that 'a moving distance' refers to a distance D indicated by the same part of the plunger 13 in the fluid feeder 1 connected to the balloon catheter 2 in a state in which the balloon 4 is completely deflated. As shown in FIG. 5, the distance D is a distance between a reference position P1 which is a starting position of the plunger 13 and a position P2 after the movement of the plunger 13 completes.

It is preferable if the reference position P1 of the plunger 13 is set such that the distal end of the plunger 13 is positioned in the vicinity of the second end 12B of the cylinder 12. In this way, a wider range of the moving distance can be achieved. However, the present invention is not limited thereto; any positions may be set as the reference position P1. According to the present embodiment, the convex portion 14A of the adjustor 14 determines the position of the plunger 13 abutting a fall-off prevention portion of the fixing portion 15 as a reference position.

As shown in FIG. 6, the difference of the moving distance which is required by the plunger 13 for further inflating a pre-inflated balloon with a desirable diameter by a predetermined amount, for example by 1 mm, increases as the diameter of the pre-inflated balloon increases. Taking into consideration the relationship described above, if a distance (space) between the adjacent projections 18 is set so as to gradually increase as increasing a diameter of the balloon, it is possible to achieve an inflation of the diameter of the balloon which corresponds to each of the projections 18 with an equal interval, for example by 1 mm. Note that a position where the engaging projections 18 is formed may be altered depending on, for example, inflation and deflation characteristics of the balloon, an interval size for achieving a desirable diameter and a desirable size of diameter to be held after inflation, or the like.

As shown in FIGS. 2 and 3, the fixing portion 15 is disposed on an outer periphery of the cylinder 12, provided with an engaged portion 19 which engages with the engaging projections 18 of the adjustor 14, a switch 20 which changes the status of engagement between the engaged portion 19 and the adjustor 14 so as to engage and disengage, and a finger resting portion for a user to rest his/her fingers at the time of the operation.

The engaged portion 19 is positioned further outward in a radial direction of the cylinder 12 with respect to the engaging projections 18, and a projection 19A is protruded so as to oppose to the engaging projections 18. When the plunger 13 slides through the inside of the cylinder 12 and a proximal side face of the engaging projections 18 and a distal side face of the projection 19A comes into contact, a positional relationship between the plunger 13 and the cylinder 12 is maintained. At this time, the inflation of the balloon 4 is maintained with the inflated diameter corresponded to the moving distance of the plunger 13 which is regulated by the engaging projections 18.

As shown in FIGS. 2 and 3, a frame-shaped fall-off prevention portion 19B is disposed on the engaged portion 19, and the adjustor 14 is passed through the fall-off prevention portion 19B. When the plunger 13 is retracted toward the proximal end, the convex portion 14A of the adjustor 14 abuts onto the fall-off prevention portion 19B at a position where the distal end of the plunger 13 comes close to the second end 12B of the cylinder 12. As a result, the plunger 13 is no longer retracted further toward the proximal end so as to prevent the plunger 13 from escaping from the cylinder 12.

One end of the switch 20 is attached to the engaged portion 19 in a freely rotating manner about the end. When the switch 20 is rotated so as to interpose between the engaged portion 19 and the adjustor 14, the engaged portion 19 and the adjustor 14 are separated so as not to engage each other. This action will be described later.

Figure 7:
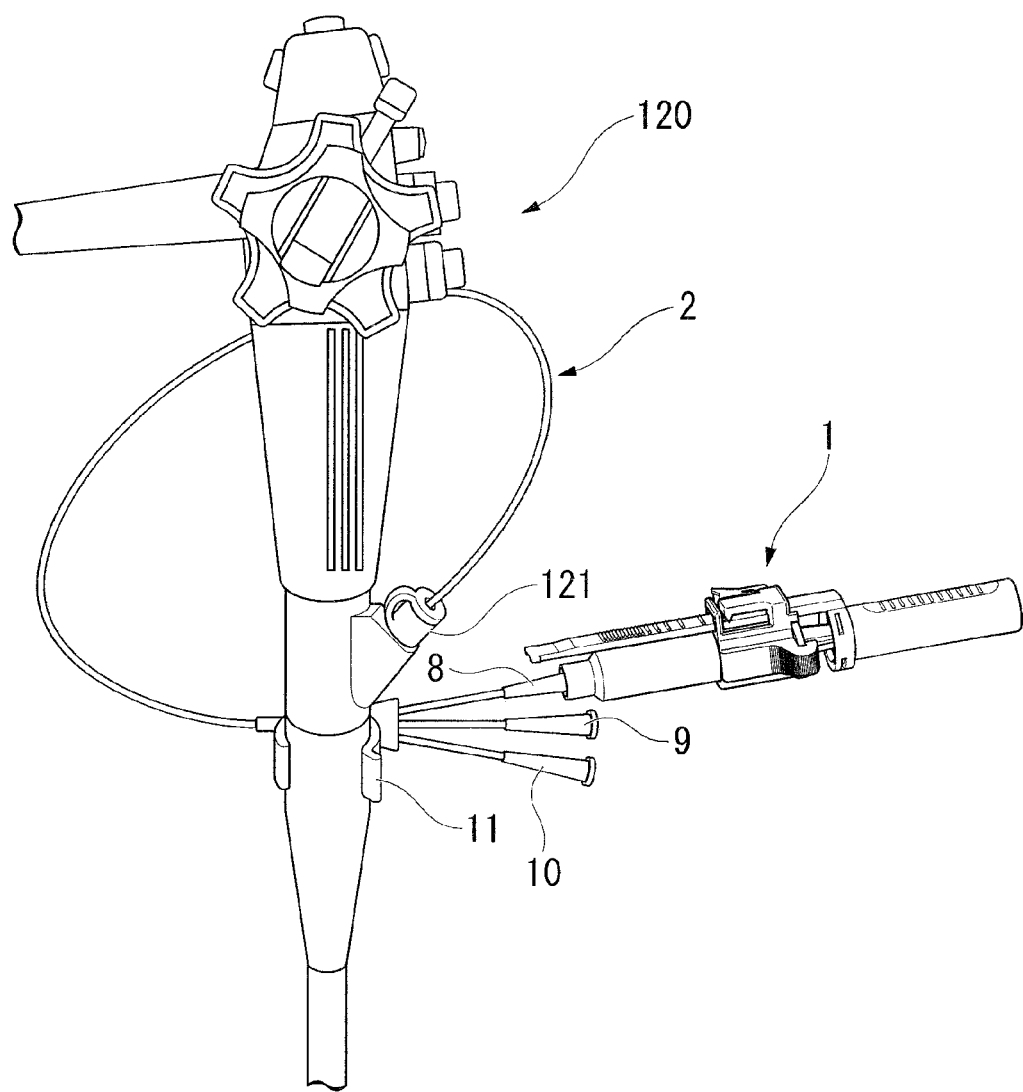
FIG. 7 shows the balloon catheter fixing onto an endoscope.

The action of the balloon catheter 2 of the present embodiment as designed above during use will now be explained with reference to FIGS. 7 though 12.

First, an endoscope is inserted into a body cavity of a patient, and the distal end thereof is moved into the vicinity of a treatment target tissue (inserting step).

At this time, the balloon catheter 2 should be ready for use. A user retracts the plunger 13 of the fluid feeder 1 toward the proximal side so as to position the plunger 13 at the reference point P1 described above, resulting a fluid flowing into the cylinder 12 to accumulate therein. Then the first end 12A of the cylinder 12 is connected to the first port 8 (connecting step).

The user inserts the distal end of the balloon catheter 2 into an instrument channel of the endoscope (not shown) from a forceps port 121 of the endoscope 120 so as to protrude the distal end of the balloon catheter 2 from a distal end of the endoscope 120. Normally, an assistant operates the fluid feeder 1 by standing close to the user; however, the user may directly operate the fluid feeder 1 by himself/herself, by fixing a handheld side of the balloon catheter 2 to the endoscope 120 with the anchor 11, as shown in FIG. 7.

Figure 8:
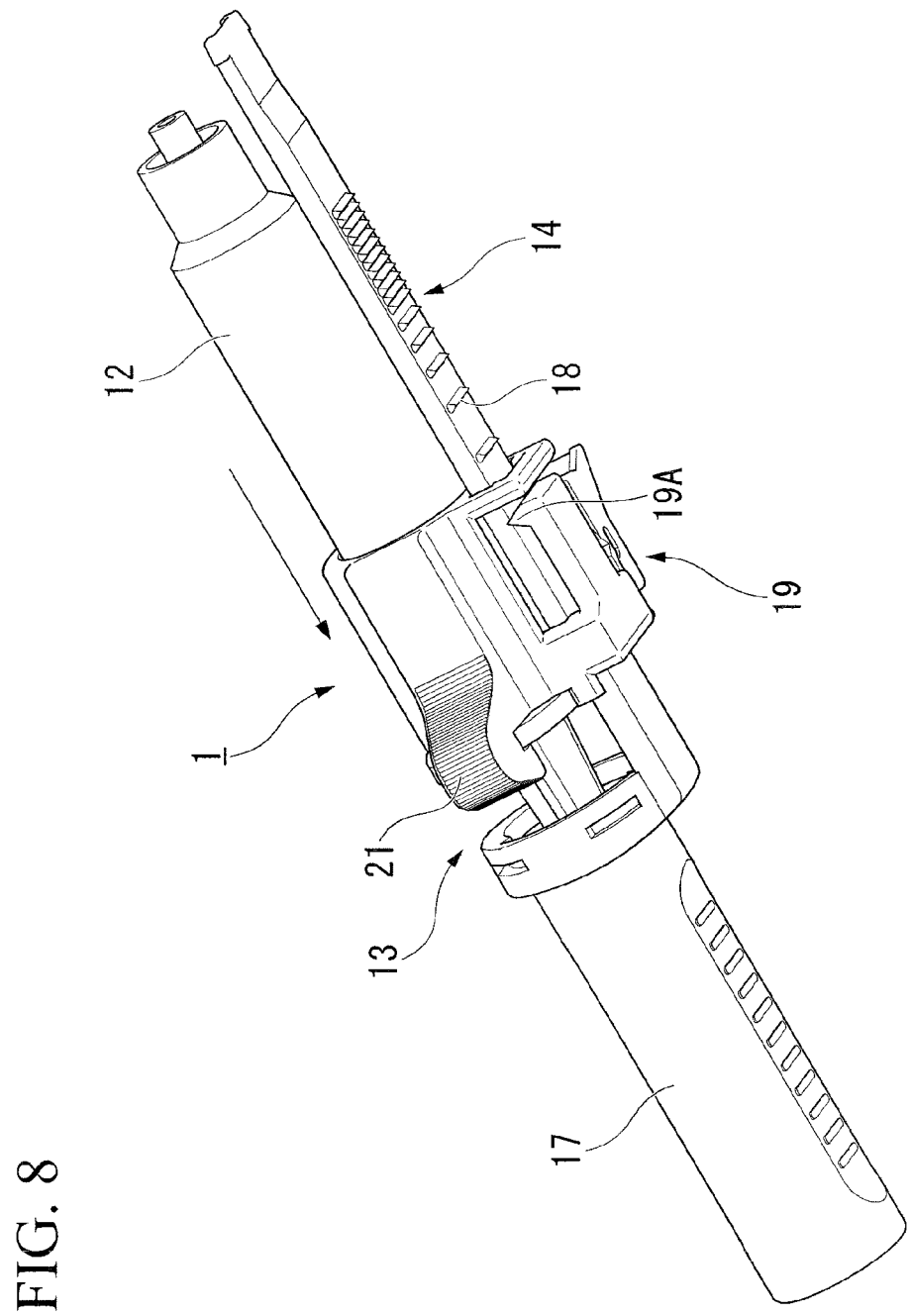
FIG. 8 shows the action of the balloon catheter 2 during use.
Figure 9:
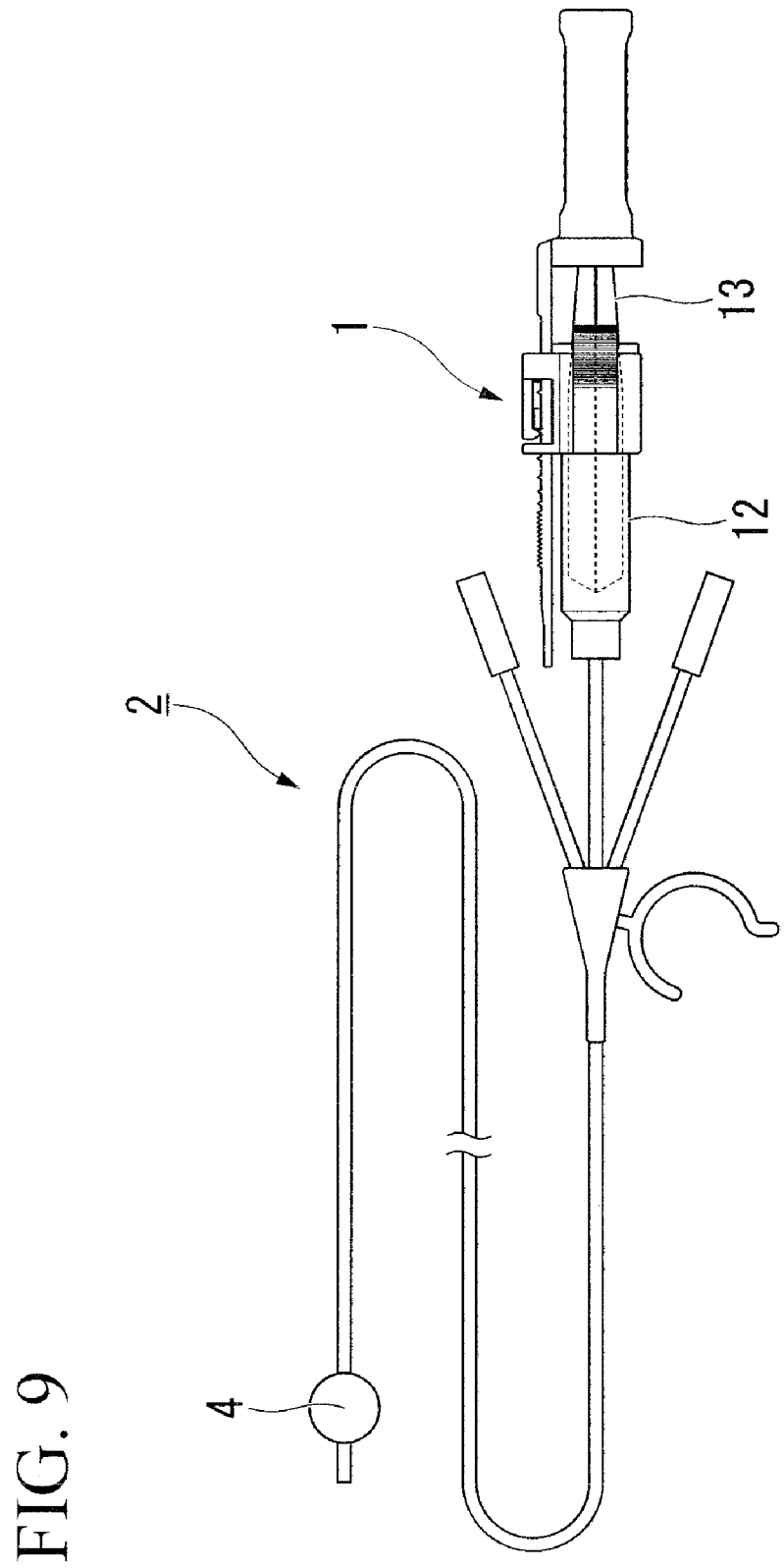
FIG. 9 shows the balloon in an inflated state.

When the balloon 4 is inflated, the user grips the grip 17 of the plunger 13 resting his/her fingers on the finger resting portion 21. As shown in FIG. 8, the plunger 13 is advanced into the cylinder 12 by pulling the cylinder 12 relative to the plunger 13. The projection 19A of the engaged portion 19 advances toward the engaging projections 18 positioned further to the proximal side, by subsequently clicking into the space between the adjacent engaging projections 18 of the adjustor 14. Simultaneously, a fluid contained in the cylinder 12 is pushed out by the plunger 13, feeding into the balloon 4 via the first port 8 and the first lumen 5 so as to inflate the balloon 4 as shown in FIG. 9 (balloon inflating step).

When the user stops the advancing operation of the plunger 13, the balloon 4 is deflated so that a pressure which pushes the fluid back to the cylinder 12 exerts onto the plunger 13. As a result, the engaging projections 18 of the adjustor 14 move toward the proximal end. Then, a proximal side slant face of the engaging projections 18 positioning closer to the distal end with respect to the projection 19A and closest to the projection 19A, comes into a contact with a distal side slant face of the projection 19A causing the plunger 13 to stop. Accordingly, the moving distance of the plunger 13 is maintained constant, so that the diameter of the balloon 4 is regulated and maintained as a set diameter size corresponding to the moving distance.

Figure 10:
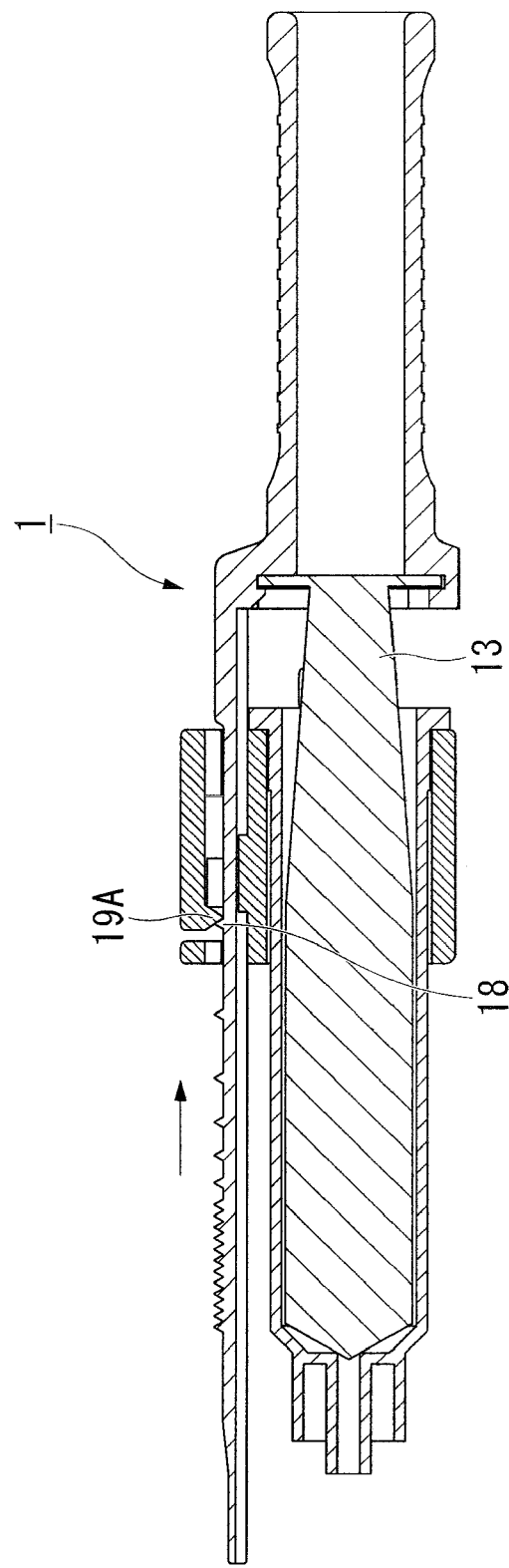
FIG. 10 shows a state in which the adjustor and the engaged portion are engaged.

As shown in FIG. 10, when the diameter of the balloon 4 is changed, the plunger 13 is advanced and retracted with respect to the cylinder 12 by the aforementioned action, so as to engage the projection 19A of the fixing portion 15 and the engaging projections 18 of a desirable position. Hence, the moving distance of the plunger 13 is regulated by the set position of the corresponding engaging projections, and the diameter of the balloon 4 changes according to the moving distance. When the plunger 13 advances and retracts and the engaged portion 19 rides over the engaging projections 18, the operator will feel a click. Hence, a user can easily recognise the number of levels shifted (in other words, a number of the engaging projections 18 in which the projection 19A has ridden over) without actually seeing a manipulation of the device. Accordingly, a diameter of the balloon 4 can be easily regulated. Further, if the plunger 13 is quickly retracted and the projection 19A of the fixing portion 15 is engaged to the engaging projections 18 at the position where the retraction of the plunger 13 is completed, in order to create a negative pressure state inside of the cylinder 12. As a result, the balloon 4 can be deflated faster (balloon diameter regulating step).

Figure 11:
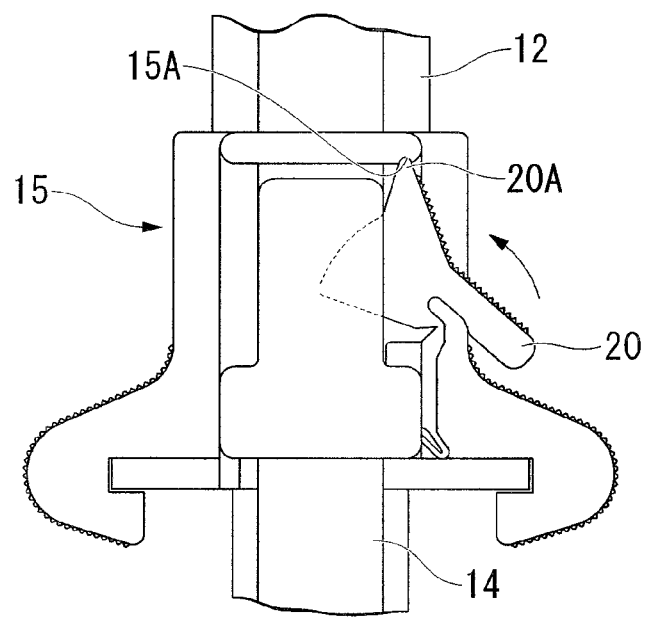
FIG. 11 shows an action of the engagement between the adjustor and the engaged portion to change to an 'OFF' state.
Figure 12:
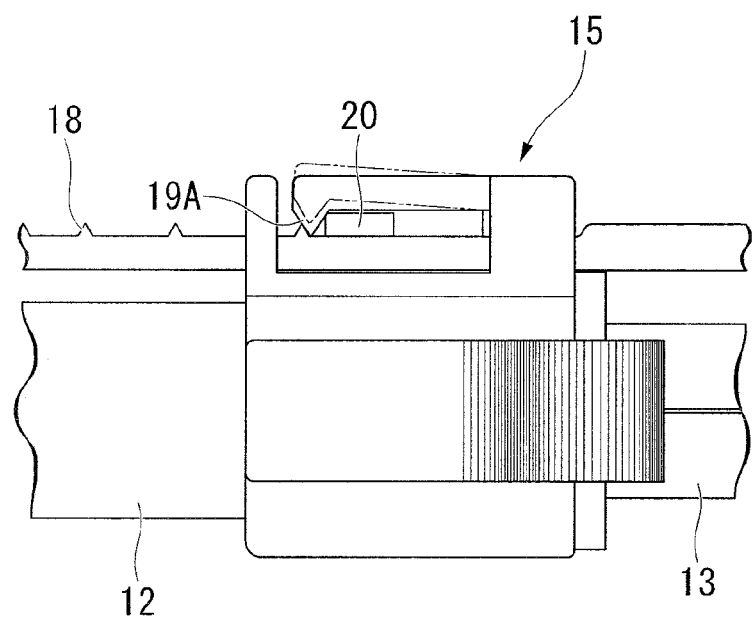
FIG. 12 shows an action of the engagement between the adjustor and the engaged portion to change to 'OFF' state.

When the balloon 4 is completely deflated, the switch 20 is pushed in so as to insert between the projection 19A and the engaging projections 18, as shown in FIGS. 11 and 12. Then as shown in FIG. 12, the projection 19A is pushed up so as to separate the projection 19A from the engaging projections 18 by the switch 20. Accordingly, the projection 19A and the engaging projections 18 are no longer engaged, changing the status of the fixing portion 15 to 'OFF'. As shown in FIG. 11, the 'OFF' state can be maintained by engaging an end portion 20A of the switch 20 onto the convex portion 15A provided on the fixing portion 15. At this 'OFF' state, the plunger 13 can be smoothly slide within the cylinder 12.

When the fixing portion 15 enters the 'OFF' state, the plunger 13 is pushed back by a deflation of the balloon 4 so that the balloon 4 completely deflates without the user operating the plunger 13. Alternatively, the 'OFF' state may be employed when the plunger 13 is pulled toward the proximal end at the aforementioned preparation stage of the balloon catheter 2 prior to use.

According to the fluid feeder 1 of the present embodiment, the moving distance of the plunger 13 is regulated by the engaging projections 18 provided on the adjustor 14 so as to inflate the diameter of the balloon 4 to a size which corresponded to the moving distance. Then, by engaging the engaging projections 18 and the projection 19A of the fixing portion 15, the inflated diameter of the balloon 4 is maintained. By virtue of the engaging action, the diameter of the balloon can be accurately regulated, even within a relatively small range of a diameter such that a diameter changes significantly with slight movement of the plunger.

Furthermore, since a distance between adjacent engaging projections is set to be increased as the moving distance of the adjustor 14 increases, it is possible to set the change of diameter (the difference by which the diameter changes) of the balloon 4 to be the same. The change of diameter is caused by clicking the engaging projections 18 which engages the projection 19A of the engaged portion 19 into the space between the next adjacent space toward the distal or proximal ends. Accordingly, the inflating diameter of the balloon 4 can be easily regulated at an equal interval, for example by 1 mm.

Furthermore, since the inflated state with a desirable diameter of the balloon 4 is maintained by the fixing portion 15, it is not necessary to provide a mechanism such as a faucet and the like, between the fluid feeder and the first port 8 for preventing a back flow of a fluid into the cylinder 12. Therefore, the structure of the balloon catheter 2 can be simplified, achieving lowering a manufacturing cost by employing the fluid feeder 1.

The present embodiment described examples in which the balloon catheter 2 was inserted into the endoscope 120. However, the present invention is not limited thereto; the balloon catheter 2 may be used without being fixed/inserted into the endoscope if a treatment is performed without the endoscope.

(Second Embodiment)

Next, a second embodiment of the present invention will be explained with reference to FIG. 13. A fluid feeder 31 according to this embodiment differs from the proceeding fluid feeder 1 with regard to the structure of the adjustor 14.

In the following description, components that are the same as the first embodiment shall be provided with the same numeric symbol and redundant description shall be omitted.

Figure 13:
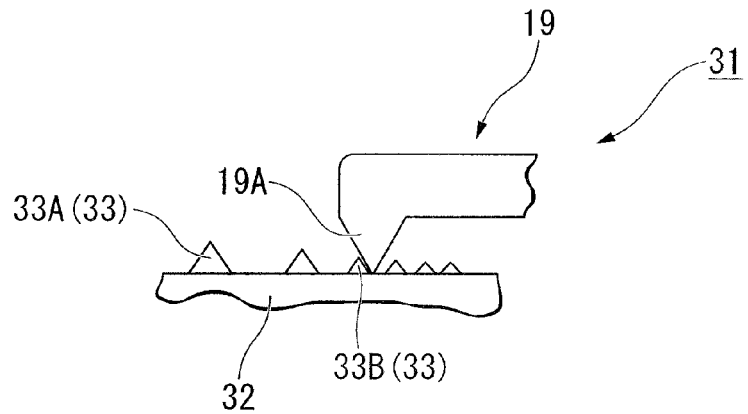
FIG. 13 is an enlarged view of the adjustor and the engaged portion of a fluid feeder according to a second embodiment of the present invention.

FIG. 13 is an enlarged view of an adjustor 32 and the engaged portion 19 of a fluid feeder 31. The size of each engaging projection 33 formed on the adjustor 32 differs and an engaging projection 33A provided on a proximal side of the adjustor 32 is larger than an engaging projection 33B provided on the distal side thereof. Accordingly, the size of the engaging projections 33 depends on its position on adjustor 32. The size increases as the position of the engaging projections 33 is closer to the proximal end of adjustor 32.

As the plunger 13 advances, the projection 19A of the engaged portion 19 engages with the engaging projections 33 positioned closer to the proximal side. As a result, more fluid is supplied into the balloon 4 so as to increase the diameter of the balloon 4. At this time, tension exerted on the balloon 4 increases so as to increase a force exerted toward the retracting direction of the plunger 13 in conjunction with the increase of the diameter of the balloon.

According to the fluid feeder 31 of the present embodiment, since the size of the engaging projections positioned closer to the proximal side of the adjustor 32 is designed to increase, an engagement force exerted between the projection 19A and the engaging projections 33 (a force required for the projection 19A rides over the engaging projections 33 abutted thereon) increases as a moving distance of the plunger 13 increases.

Therefore, although a stronger force exerts to the direction in which the plunger 13 is retracted with respect to the cylinder 12 by increasing a diameter of the balloon 4, the positional relationship between the plunger 13 and the cylinder 12 is maintained so as to maintain the diameter of balloon.

(Third Embodiment)

Next, a third embodiment of the present invention will be explained with reference to FIG. 17A through FIG. 28.

FIG. 17A is a front view showing a fluid feeder supporting device 201 according to the present embodiment. The fluid feeder supporting device 201 is detachably attached to the cylinder 12 and the plunger main body 16, and includes a fixing portion 215 detachably attached to the cylinder 12 and the adjustor 14 detachably attached to the plunger main body 16. Furthermore, a grip 217 is integrally formed with the adjustor 14.

the fixing portion 215 has its structure corresponding to the fixing portion 15 of the first embodiment; however, the structure of the fixing portion 215 differs from that of the fixing portion 15 with respect to the following. First, a through hole 215A having its inner diameter substantially same as an outer diameter of the cylinder 12 is formed on the fixing portion 215. A pair of finger resting portions 221 is disposed on the fixing portion protruding to an outer radial direction. At both sides of the first end 12A and the second end 12B of the cylinder 12, a curved slant face with respect to the central axis of the through hole 215A of a finger resting portion 221 protrudes to an outer radial direction. A plurality of convex and concave shapes are formed on the surface of the curved slant face, preventing a user's finger from slipping when he/she places their finger thereon. Note that the finger resting portion 221 may protrude to an outer radial direction in a straight line extending from the fixing portion 215. Also, the finger resting portion 221 projecting outward in the radial direction from the fixing portion 215 is formed at both sides of the first end 12A and the second end 12B of the cylinder 12. Also, the finger resting portion 221 is placed toward the engaged portion 19 side on a position axially offset with respect to a central axis O2 of the through hole 215A when seen in a plain view. In the present embodiment, a position of the finger resting portion 221 and a position of a central axis of the grip 217 when seeing in a plain view are aligned along the longitudinal direction.

A portion of a force applied to the finger resting portion 221 in order to cause advancing and retracting movement of the adjustor 14 relative to the fixing portion 215 is converted to a rotational force around a connecting point (or connecting line) between the engaging projections 18 of the adjustor 14 and the projection 19A of the engaged portion 19 (or the connecting point or the connecting line being a central axis of the rotational force). At this time, moment becomes larger as the force applied to the finger resting portion 221 increases, then a bending moment is applied to adjustor 14. When an excessive bending moment is exerted onto the adjustor 14, the adjustor 14 is elastically deformed. As a result, a central axis of the plunger main body 16 is often deviated from the central axis O2 of the cylinder 12. The deviation of the central axes may become a cause of dispersing a force to a different vector from a vector (the force) originally required for the advancing and retracting movement. Furthermore, the deviation of the central axes is prone to happen if the position of the finger resting portion 221 is further from the connecting point of each of the engaging projections 18 and the projection 19A. Therefore, if the finger resting portion 221 is not placed on a position axially offset with respect to the central axis O2 of the cylinder 12, there is a possibility of deteriorating the operability due to increasing a resistance between the cylinder 12 and the plunger main body 16 when they advance and retract relative to each other.

As described above, since the finger resting portion 221 is placed on a position axially offset with respect to the central axis O2 of the cylinder 12, and the finger resting portion 221 is disposed closer to the connecting point so as to set a turning radius when the rotational force is generated to be short; based on the force applied to the finger resting portion 221, a torque about the connecting point as a rotational axis will be reduced. Accordingly, the deformation of the adjustor 14 is suppressed so as to prevent the central axis of the plunger main body 16 from deviating away from the central axis O2 of the cylinder 12. In addition, in theory, the torque should be decreased as the deviated distance (the offset amount) from the central axis O2 of the cylinder 12 is increased until the finger resting portion 221 aligns to a longitudinal axis of the adjustor 14 when seeing in the plain view.

FIG. 17B is a plain view showing a fluid feeder supporting device 201 according to the present embodiment. As shown in FIG. 17B, a depression 222 which can accommodate the flange 12C of the cylinder 12 thereinto is formed on the finger resting portion 221. In particular, in the fixing portion 215, the depression 222 is formed on a section of one of each side of a pair of the index finger resting portions 221 such that each of the sides face each other via the through hole 215A. The depression 222 has its depression depth substantially the same as the thickness of the flange 12C in the axial direction of the through hole 215A, and has enough width to allow the flange 12C to be inserted due to a rotating movement of the cylinder 12 in a circumferential direction. Thus, the depression 222 has a pair of walls facing each other such that it separates from the end of the through hole 215A in the axial direction, and substantially orthogonal to the central axis of the through hole 215A. By abutting the flange 12C onto the wall of the depression 222 and the end of the through hole 215A, the advancing and retracting movement of the cylinder 12 in the axial direction is regulated.

When the flange 12C is inserted into the depression 222, the flange 12C is supported by the wall of the depression 222, and then the cylinder 12 is supported at a determined position in a direction of the central axis O2. Furthermore, a projection 223 which can contact the flange 12C of the cylinder 12 is formed on the fixing portion 215. The flange 12C which is capable of rotating around the central axis O2 inside of the through hole 215A is supported by the projection 223 at a determined position where the flange 12C is inserted into the depression 222. A detailed attachment mechanism of the cylinder 12 onto the fixing portion 21 will be described later.

FIG. 17C is a cross-sectional view as seen from a line A-A of FIG. 17A. As shown in FIG. 17C, in the present embodiment, a marking M (denoting with the same referenced symbol in the figure) is marked on the outer surface of the cylinder 12 at two locations directly opposing each other in the radial direction. Since the cylinder 12 exhibits a rotating characteristic of 180 degrees around the central axis O2, the direction in which the cylinder 12 faces the user may be opposite depending on the attachment direction of the cylinder 12 with respect to the first port 8. Since the markings M are marked on the outer surface of the cylinder 12 at two locations directly opposing each other in the radial direction, the user can visually confirm the marking M regardless the direction of the attachment of the cylinder 12 with respect to the first port 8.

The marking M also indicates the size of an inflated diameter of the balloon 4 corresponding to the type of the cylinder 12, such that the balloon 4 can be inflated without a risk of rupturing. For example, a mark "20" shown in FIG. 17A indicates a cylinder having a balloon with the maximum inflated diameter of 20 mm, and also indicates that a diameter of the balloon becomes 20 mm when the plunger main body 16 is inserted up to the position of the marking M with a method described later. Thereby, the marking M has both effects of preventing a user from selecting an incorrect combination of the cylinder 12 and the balloon 4, and informing the user of the diameter of the balloon 4 when in use.

Furthermore, it is preferable that the marking M is marked with a base color M1 and a mark M2 (such as a letter or a symbol) which has a higher legibility, and the mark M2 is colored onto the base color M1. As for a combination of the base color M1 and the mark M2, any combination with a high contrast color may be selected; for example, combinations such as white as the base color M1 and orange as the mark M2, blue as the base color M1 and yellow as the mark M2, and the like may be selected. Furthermore, the marking method of the marking M is not limited thereto; for example, the marking M may be printed onto the outer surface of the cylinder 12, or the marking M may be cut out from a sheet having adhesive on one side and stick the cut out portion of the marking M onto the outer surface of the cylinder 12.

As further shown in FIG. 17A, different from the grip 17 of the first embodiment, the grip 217 is formed in a position axially offset with respect to the central axis of the plunger main body 16 (which is the central axis O2 of the cylinder 12) toward the engaged portion 19 side when seen in a front view. In the present embodiment, the grip 217 has a rod member 217C which can be a filled rod member or a tubular rod member. A central axis O1 of the rod member 217C is different from the central axis O2 of the plunger main body 16 and the cylinder 12; they do not align in a horizontal direction. The rod member 217C has a flat surface by cutting a portion of the outer surface thereof. The flat surface has its function as a stopper preventing the rod member 217 from rotating about the central axis O1 when a user holds the rod member 217C. In this embodiment, the flat surface is formed on the outer surface of the rod member 217C on planes opposing each other so as to function as a stopper.

As shown in FIG. 17B, a index finger resting portion 217B is formed on the grip 217 along the central axis O2 when seen in a plain view. The index finger resting portion 217B forms in a substantially C- or U-shape having one portion open so as to assist a user to hold the grip 217. In this embodiment, the index finger resting portion 217B is in a substantially circular shape which is a part of a circular arc abutting a base 230 which is connected to a projected end 16A, and has its thickness in an orthogonal direction to a plane where the circular arc exists. In addition, the thickness of the index finger resting portion 217B is formed less than the diameter of the rod member 217C, and a gentle tapered portion continues from the index finger resting portion 217B to the rod member 217C.

An end of the index finger resting portion 217B which is opposite to another end connecting to the rod member 217C extends outward from the base 230 along the substantially circular shape of the index finger resting portion 217B. Since two ends of the substantially circular shape face the opposite direction of a position of the base 230 to the plunger main body 16, the index finger resting portion 217B provides a suitable curved shape for resting a finger, in particular the shape is suitable for fitting to a ball of a thumb.

Furthermore, a central axis of the substantially circular shape of the index finger resting portion 217B has a positional relationship which is orthogonal to the central axis O2 of the plunger main body 16 and faces to the thickness direction of the adjustor 14.

Therefore, the grip 217 forms a J-shape which is detachably connected to the plunger main body 16 at the index finger resting portion 217B.

The finger resting portion 221 and the index finger resting portion 217B are disposed so as to exist on a same plane when the fixing portion 215 and the adjustor 14 are connected. In other words, a positional relationship of the finger resting portions 221 and the index finger resting portion 217B is such that each of the finger resting portions 221 protrudes to the outer radial direction of the cylinder 12 in a plane orthogonal to the central axis O1, and the substantial circular shape of the index finger resting portion 217B is positioned on the same plain where the finger resting portions 221 exists.

The present embodiment has two positional relationships in holding the grip 217 and the finger resting portions 221 with a finger. The first positional relationship is to grip the fluid feeder supporting device 201 with the rod member 217C of the grip 217 and the finger resting portions 221.

In this first positional relationship, the thumb and the index finger of a user are placed on respective finger resting portions 221, and the fingers are well fitted on the surface of the finger resting portions 221 with a friction. With respect to the finger resting portions 221, the fingers of the user can be placed on either sides of the first end 12A or the second end 12B of the cylinder 12 depending on the direction of a relative movement of the plunger main body 16 and the cylinder 12.

For example, when the plunger main body 16 is moved to a direction in which the plunger main body 16 is pushed into the cylinder 12, the fingers of the user are placed on the first end 12A of the finger resting portions 221.

On the other hand, when the plunger main body 16 is moved to a direction in which the plunger main body 16 is pulled out from the cylinder 12, the fingers of the user are placed on the first end 12B of the finger resting portions 221.

At this time, in both cases above, a middle, a annular and a little fingers are sequentially placed on a grip 217 from a direction of the index finger resting portions 217B to the rod member 217C so as to grip the rod member 217C.

The second positional relationship of the fingers for gripping the grip 217 and the finger resting portions 221 is to hold the fluid feeder supporting device 201 with the index finger resting portion 217B and the finger resting portions 221.

With this second positional relationship, at least one or more of the second to little fingers of the user are placed on each of the finger resting portions 221, and the fingers are attached on the surface of the finger resting portions 221 with a friction. At this time, the first end 12A of the cylinder 12 in the vicinity of the finger resting portions 221 is used.

In the index finger resting portion 217B of the grip 217, the thumb of the user is placed on a position opposite to the projected end 16A of the plunger main body 16. Since the index finger resting portion 217B forms in a substantial U-shape or C-shape, when the thumb is moved with compressing the index finger resting portion 217B toward the plunger main body 16 at a position in which the thumb is placed on the index finger resting portion 217B, a deviation of a position of the thumb is prevented such that the position of the thumb is determined so as to face the projected end 16A of the plunger main body 16 in a manner of following the curved shape of the index finger resting portion 217B.

The positional relationship of hooking the thumb to the index finger resting portion 217B is solely used in the relative movement of the plunger main body 16 with respect to the cylinder 12 when the plunger main body 16 is moved to the direction in which the plunger main body 16 is compressed into the cylinder 12.

A gripping method of the grip 217 and the finger resting portions 221 of the fluid feeder supporting device 201 of the present embodiment when in use will be described later.

Furthermore, the shape of the index finger resting portion 217B is not limited to the shapes described above; any shape may be employed as long as the index finger resting portion 217B is positioned opposite to the cylinder via the plunger main body 16, and is positioned in the vicinity of the plunger main body 16. In other words, it is preferable to construct the shape of the index finger resting portion 217B such that the positional relationship of user's fingers when the user places his/her fingers on the finger resting portions 221 and the index finger resting portion 217B becomes the same positional relationship when the user places his/her fingers on the flange 12C of the cylinder 12 and the projected end 16A of the plunger main body 16.

Figure 18A:
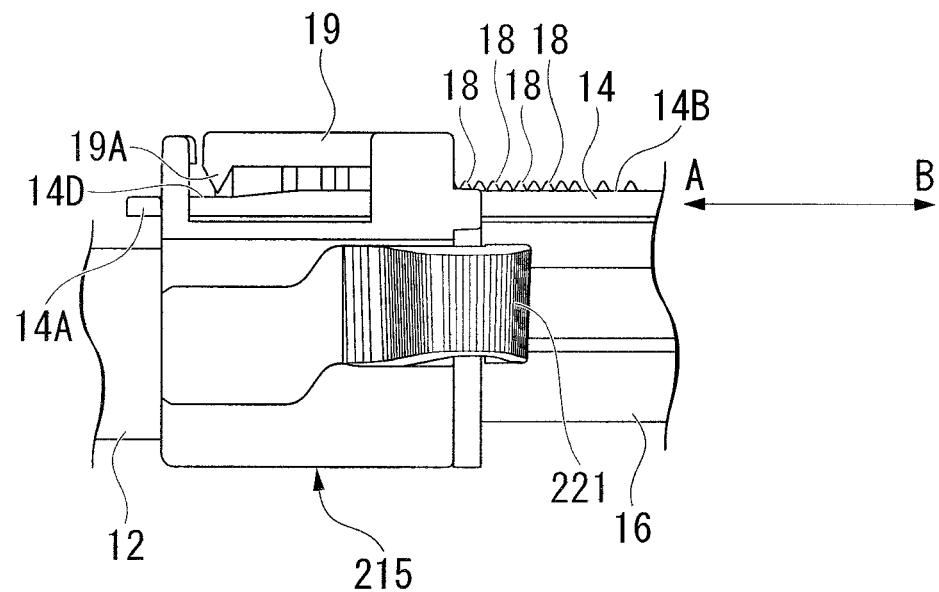
FIG. 18A is an enlarged front view showing a portion of the fluid feeder supporting device.

FIG. 18A is an enlarged front view showing the fixing portion 215 of the fluid feeder supporting device 201. As shown in FIG. 18A, the adjustor 14 is inserted through the fixing portion 215 permitting the advancing and retracting movements of fixing portion 215 relative to the longitudinal direction of the adjustor 14.

One end (a first end) of the engaged portion 19 is fixed to the fixing portion 215 and another end (a second end) extends to a direction in which the plunger main body 16 is inserted into the cylinder 12. The projection 19A is formed on the second end of the engaged portion 19 so as to abut the engaging projections 18 of the adjustor 14. The fixing portion 215 and the engaged portion 19 are integrally formed, and the engaged portion 19 can be elastically deformed like a plate spring due to its elasticity in response to a bending moment caused when the projection 19A comes into contact to the engaging projections 18. When the projection 19A of the engaged portion 19 and the engaging projections 18 of the adjustor 14 comes into contact and they are pressed each other, a different degree of a force is required for the projection 19A rides over the engaging projections 18 by advancing and retracting the engaged portion 19 and the adjustor 14 relative to each other. This is because, for example, the projection 19A is pulled toward the second end of the engaged portion 19 by the engaging projections 18 when the projection 19A rides over the engaging projections 18 by the movement of the plunger main body 16 toward the direction in which the plunger 13 is inserted into the cylinder 12 (hereinafter, called a direction A). The traction caused when the projection 19A is pulled toward is converted into a pressing force which generates a bending moment of the projection 19A by both of the slant faces of the projection 19A and the engaging projections 18. On the other hand, when the projection 19A rides over the engaging projections 18 as a result of the plunger 13 moving toward a direction in which the plunger 13 is detached from the cylinder 12, the projection 19A is pressed toward the first end of the engaged portion 19 by the engaging projections 18. As a result, a compression force is applied onto the projection 19A. This compression force prevents the engaged portion 19 from deforming toward a direction in which the engaged portion 19 escapes from the engaging projections 18, having a higher resistance compared when the plunger moves toward the direction A.

With respect to an operability of advancing and retracting movement of the fixing portion 215 and the adjustor 14, a small force is preferred for a linear movement to the direction A for inflating the balloon 4, however, more force is preferred in a linear movement opposite to the direction A, since it is required to maintain the engagement between the projection 19A and the engaging projections 18 against the pressure transmitted from the balloon 4.

as described above, different degrees of force are required depending on the directions of advancing and retracting movements of the engaged portion 19 and the adjustor 14 for the projection 19A riding over the engaging projections 18. This is important for a smooth inflation and deflation operation of the balloon 4 disposed on the balloon catheter 2. In particular, when the fixing portion 215 and the adjustor 14 advance and retract as a result of the projection 19A riding over the engaging projections 18, a smaller force which is generated upon the movement is used for inflating operation of the balloon 4, and a larger force is used for the deflating operation of the balloon 4. This is how the force required in the inflation and deflation of the balloon by the user is balanced.

Figure 18B:
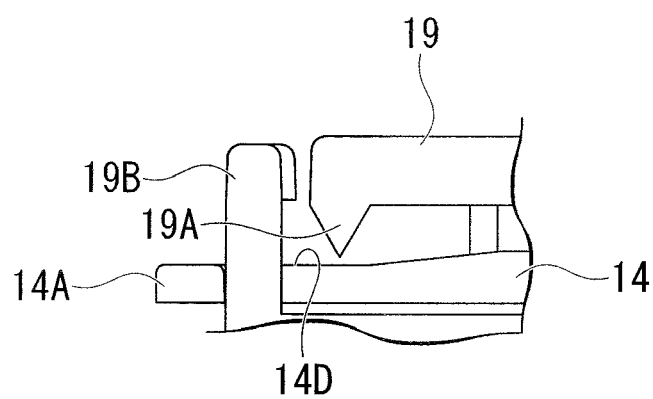
FIG. 18B is an enlarged front view of further enlarging a portion shown in FIG. 18A.

FIG. 18B is an enlarged front view of further enlarging FIG. 18A showing a portion in the vicinity of the projection 19A. As shown in FIG. 18B, a thin portion 14D which is thinner than the grip 217 side of the adjustor 14 is provided on the adjustor 14. No projections such as the engaging projections 18 are formed on the thin portion 14D, but a plane opposed to the projection 19A is formed while maintaining a space therebetween is formed on the thin portion 14D. The purpose of the thin portion 14D is to locate the adjustor 14 and the projection 19A with a space therebetween so as to effectively sterilize the fluid feeder supporting device while the fixing portion 215 and the adjustor 14 are fixed thereonto. By having the space therebetween, the sterilizing agents such as UV-rays, gamma rays, ethylene oxide gas, high-pressure steam and the like effectively reach the outer surface of the members disposed on the fluid feeder supporting device.

Figure 19A:
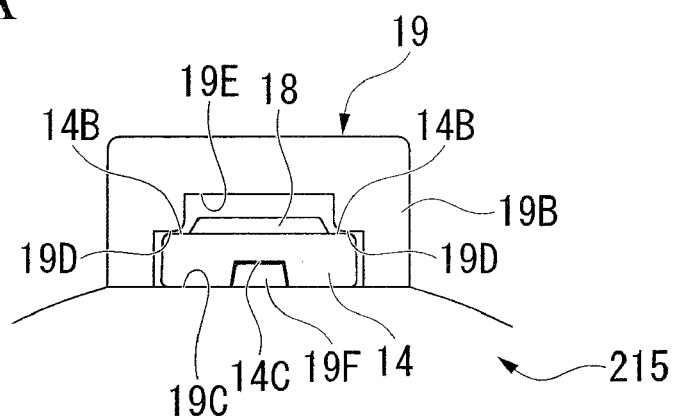
FIG. 19A is an enlarged left side view of a portion of the fluid feeder supporting device.

FIG. 19A is an enlarged left side view of the adjustor 14 and the fixing portion 215 in a fixed position. As shown in FIG. 19A, the fall-off prevention portion 19B in which the adjustor 14 is passed through is disposed on the fixing portion 215 (refers to FIG. 18B). A through hole is also formed on the fall-off prevention portion 19B, having its shape substantially the same as the adjustor 14 when seen in a left side view. The fall-off prevention portion 19B is also provided with a sliding plane 19D in which both sides of an upper plane 14B of the adjustor 14 along the longitudinal direction are slidable; a relief portion 19E which is formed higher than the height of the engaging projections 18 and is interposed between each of the sliding planes 19D; a sliding plane 19C opposing to the sliding plane 19D; and a thread portion 19F which protrudes to a substantially middle of the sliding plane 19C when seeing in a left side view shown in FIG. 19A and is engaged with the adjustor 14. The thread portion 19F supports the adjustor 14 and is slidably movable with respect to the adjustor 14.

The sliding planes 19C and 19D have a clearance abutting the adjustor 14 but slidable with respect to the adjustor 14, so as to control a deviation of the adjustor 14 in a vertical direction when seen in a left side view shown in FIG. 19A and guide the adjustor 14. When the sliding planes 19C and 19D and the adjustor 14 advance and retract with respect to the fixing portion 215 in a longitudinal direction, the thread portion 19F is capable to control a deviation of the adjustor 14 in a vertical direction when seen in a left side view shown in FIG. 19A and guide the adjustor 14 so as to direct the advance and retract movements to the longitudinal direction of the adjustor 14.

Figure 19B:
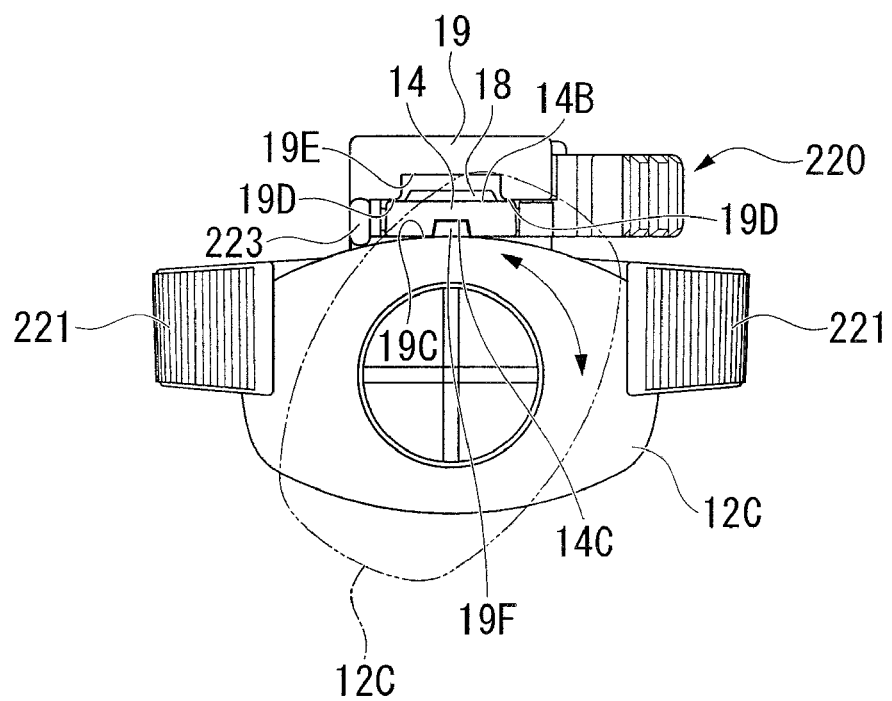
FIG. 19B is an enlarged right side view of a portion of the fluid feeder supporting device.

FIG. 19B is an enlarged right side view of the adjustor 14 and the fixing portion 215 are in a fixed position. As shown in FIG. 19B, similar to the fall-off prevention portion 19B, the engaged portion 19 also includes sliding planes 19C and 19D, and a relief portion 19E which are same size to those provided on the fall-off prevention portion 19B, and support the adjustor 14.

A track shown with a two-dot chain line represents an outer shape of the flange 12 when it is rotated around the central axis O2 of the cylinder 12. The cylinder 12 is inserted into the through hole 215A (referring to FIG. 17A) with a positional relationship shown with the two-dot chain line prior to fixing the adjustor to the fixing portion 215. At this time, the flange 12C is inserted into the through hole 215A without being interrupted by a projection 223 and a recessed portion 222 when seen in a right side view as shown in FIG. 19B. Thereafter, each end of the flange 12C is inserted into respective recessed portions 222 when the cylinder 12 is rotated around the central axis O2.

Figure 20A:
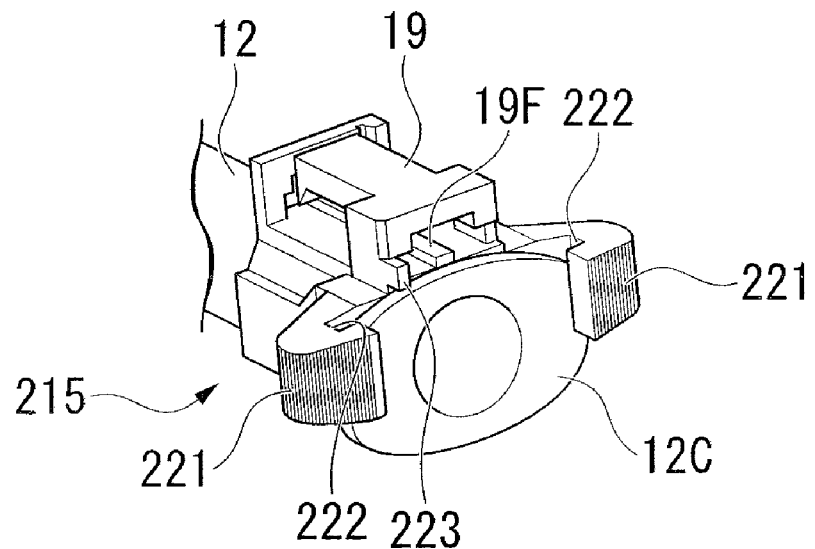
FIG. 20A is an enlarged perspective view of a portion of the fluid feeder supporting device.

FIG. 20A is an enlarged perspective view of the fixing portion 215 when each end of the flange 12C is inserted into the respective recessed portions 222. As shown in FIG. 20A, when both ends of the flange 12C are inserted into the recessed portions 222, a peripheral edge of the flange 12C abuts an outer surface of the projection 223 so that the flange 12C is supported by the projection 223.

Figure 20B:
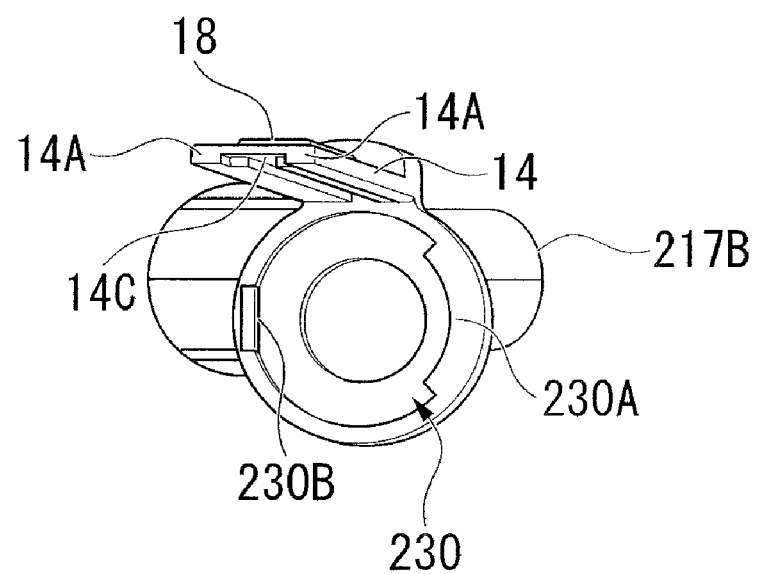
FIG. 20B is an enlarged perspective view of a portion of the fluid feeder supporting device.

FIG. 20B is an enlarged perspective view of the adjustor 14 prior to the plunger main body 16 being attached thereto. As shown in FIG. 20B, a base 230 used for attaching the plunger main body 16 is provided on the adjustor 14. A plurality of claws 230A and 230B protruded from an outer periphery to an inner side of the base 230 are provided on the base 230.

Figure 21A:
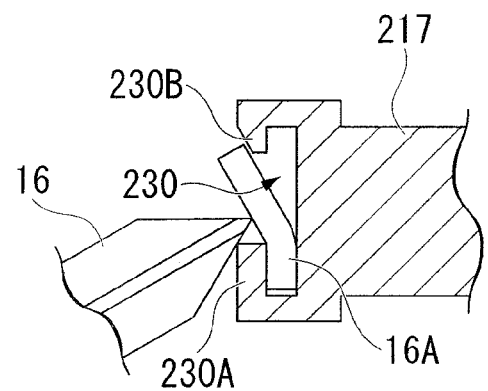
FIG. 21A is an enlarged front view that includes a cross-section through a portion of the fluid feeder supporting device.
Figure 21B:
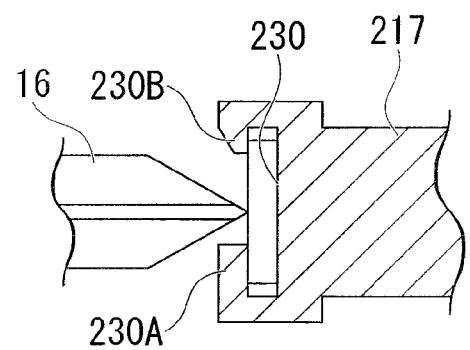
FIG. 21B is an enlarged front view that includes a cross-section through a portion of the fluid feeder supporting device

FIG. 21A and FIG. 21AB are enlarged front views of a cross-section through a portion of the base 230 during an attachment step of the adjustor 14 to the plunger main body 16.

As shown in FIG. 21A, a notch is formed on one of the claws, for example on 230B. The notch is used for hooking the projected end 16A, such that the projected end 16A extended from the cylinder 12 is hooked onto the claw 230A first, then pressed onto the claw 230B so as to be elastically deformed for allowing the projected end 16A to be hooked. Since the claw 230B is provided with the notch, the projected end 16A is elastically deformed toward an inner radial direction of the base 230 by a force in which the projected end 16A is pressed onto the claw 230B. As the result, the projected end 16A can easily be engaged with the claw 230B. In addition, a space is provided between the projected end 16A and the base 230 permitting the sterilization effectively in a similar manner to the space provided between the projection 19A and the thin portion 14D as described above.

Figure 22:
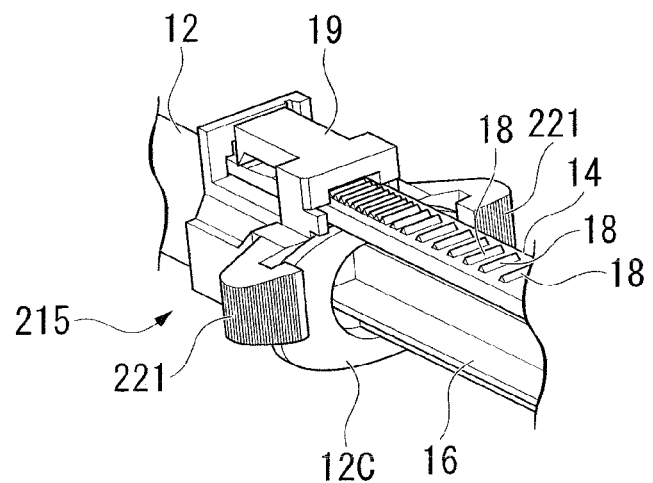
FIG. 22 is an enlarged perspective view of a portion of the fluid feeder supporting device.

FIG. 22 is an enlarged perspective view of the fixing portion 215 attached with the adjustor 14 and the plunger main body 16. As shown in FIG. 22, with the adjustor 14 being inserted into the fixing portion 215, the peripheral edge of the flange 12C abuts the adjustor 14 when the cylinder 12 is rotated so as to regulate the rotary movement. Thus, the flange 12C does not escape from the recessed portion 222 since the flange 12C is supported by the projection 223 and the adjustor 14.

Figure 23A:
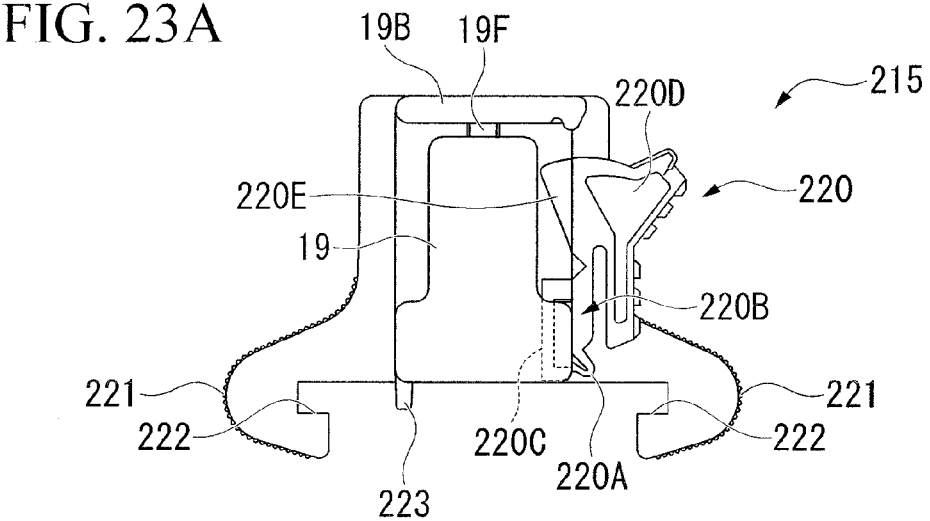
FIGS. 23A to 23C are enlarged plain views showing a portion of the fluid feeder supporting device.
Figure 23B:
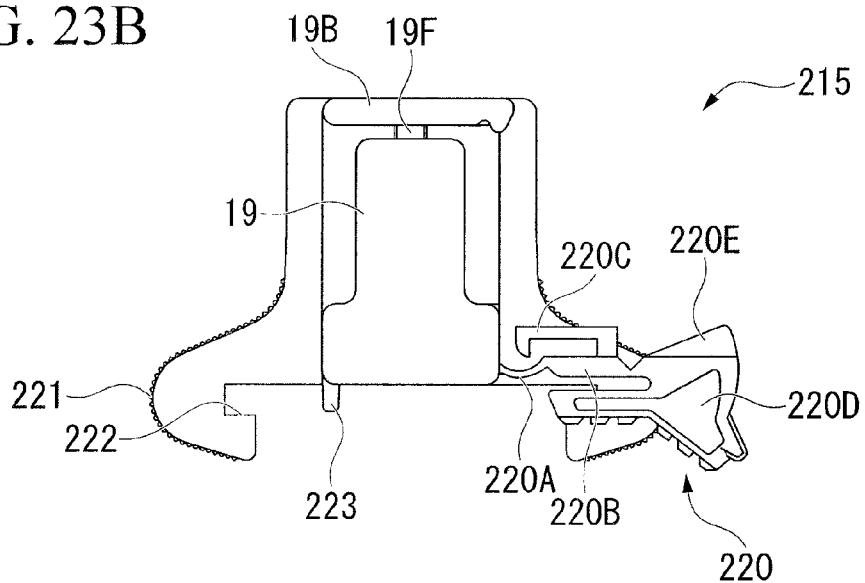
Figure 23C:
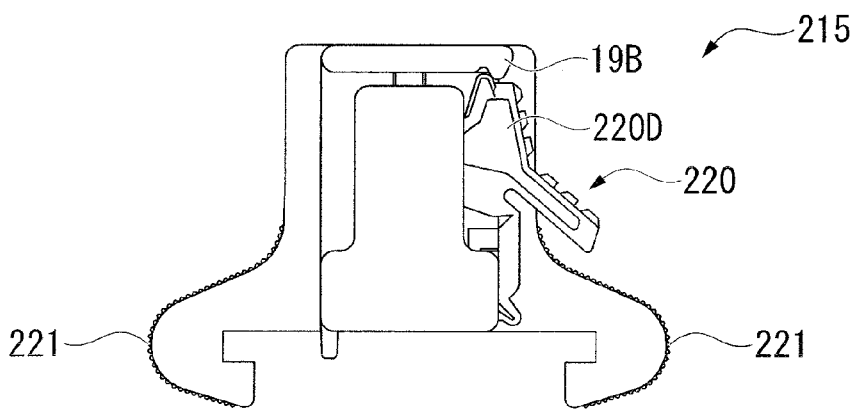

FIGS. 23A to 23C are enlarged plain views of the fixing portion 215. Note that FIGS. 23A to 23C only show the fixing portion 215 and other portions integrally mounted therewith, and illustration of remaining components is omitted. FIGS. 23A and 23C show an outer shape of the fixing portion 215 after being fixed and FIG. 23B shows the outer shape of the fixing portion 215 prior to being fixed.

As shown in FIGS. 23A and 23B, a switch 220 is disposed on the fixing portion 215 via a flexible hinge 220A. The fixing portion 215, the hinge 220A and the switch 220 are integrally mounted and formed of a same material.

The switch 220 includes a switch proximal end portion 220B adjacent to the hinge 220A, a hook 220C which fixes the switch proximal end portion 220B onto the fixing portion 215, and a switch distal end portion 220D which freely oscillates with respect to the switch proximal end portion 220B. A boundary between the switch proximal end portion 220B and the switch distal end portion 220D exhibits high flexibility by increasing the thickness at the boundary so as to act as a fulcrum of the oscillation movement of the switch distal end portion 220D when in use.

Furthermore, a wedged portion 220E having a wedge shape is formed on the switch distal end portion 220D, that is inserted between the adjustor 14 and the engaged portion 19. The wedged portion 220E releases an engagement between the engaging projections 18 and the projection 19 by being inserted into a space between the adjustor 14 and the engaged portion 19 so as to open the space thereof.

As shown in FIG. 23C, both of a distal end of the switch distal end portion 220D and the fall-off prevention portion 19B are formed in a hook shape so as to fix to each other. Thereby, the wedged portion 220E can be fixed at the space between the adjustor 14 and the engaged portion 19. Thus, the user can recognize whether or not the wedged portion 220E is properly inserted into the space between the adjustor 14 and the engaged portion 19 by feeling a click.

Figure 29:
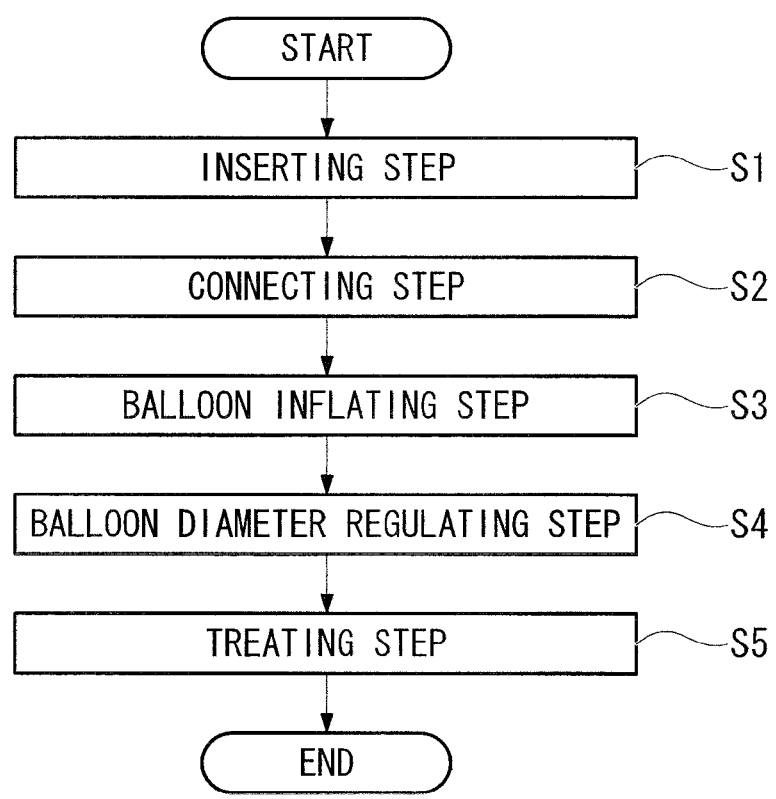
FIG. 29 is a flowchart showing a fluid feeding method of the third embodiment of the present invention.

An appropriate method of use and the action of the fluid feeder supporting device shall now be described in line with a medical procedure of removing a gall stone or biliary sludge from the bile duct of a patient as shown in FIG. 24 through FIG. 29. Each of FIG. 24 to FIG. 28 shows an action of the fluid feeder supporting device during use, and FIG. 29 is a flowchart showing a fluid feeding method of the present embodiment.

The fluid feeder supporting device 201 is brought to the user after being sterilized in a state in which the cylinder 12 and the plunger main body 16 are attached thereonto. Hereinafter, the cylinder 12 and the plunger main body 16 are fitted onto the fluid feeder supporting device 201 is called a fluid feeder 1201.

Figure 24:
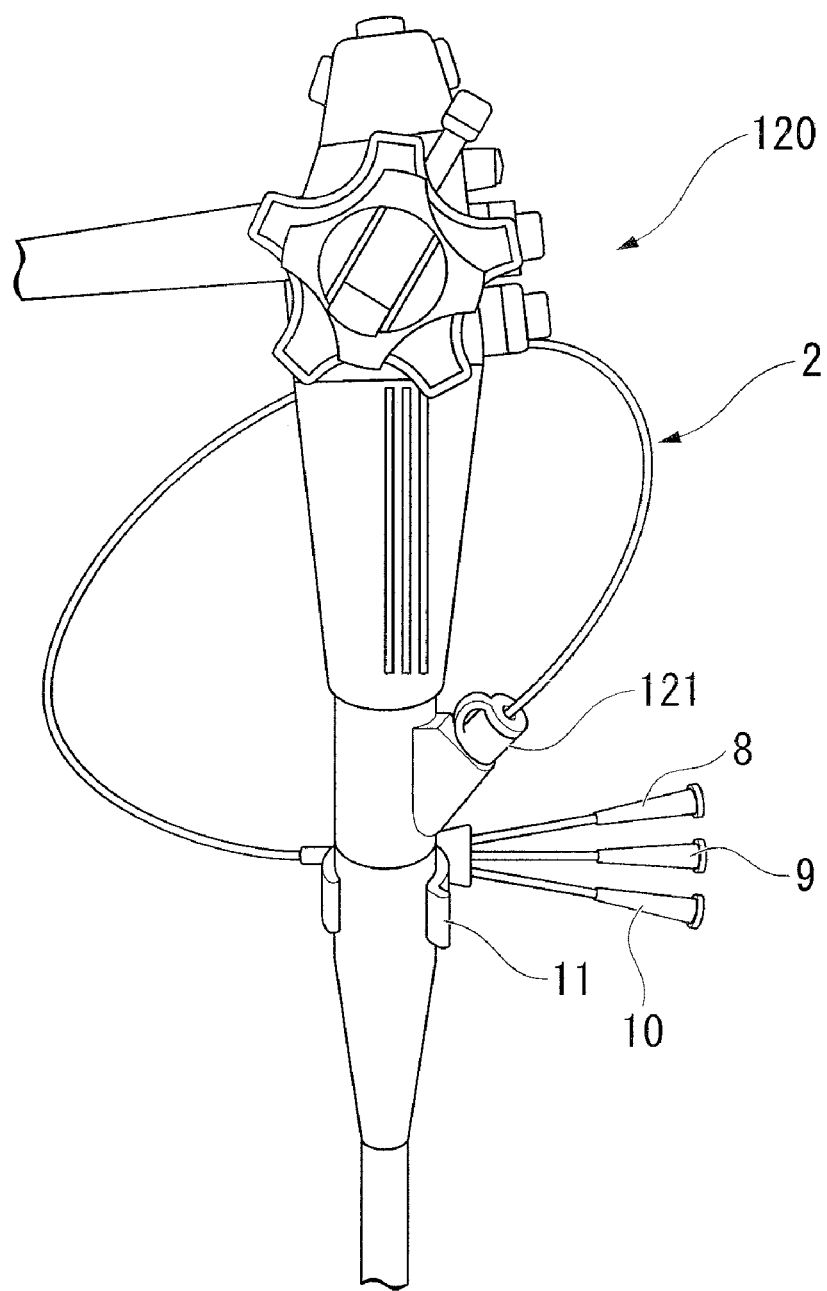
FIG. 24 shows an action of the fluid feeder supporting device during use.

First, an endoscope 120 is inserted into a body cavity via a natural orifice of a patient by a conventional method, and the distal end thereof is moved into the duodenum. Next, while an image of duodenal papilla being captured within a field of view of the endoscope 120, the distal end of the balloon catheter 2 is inserted into the instrument channel from the forceps port 121 of the endoscope 120 so as to protrude the distal end of the balloon catheter 2 from a distal end of the endoscope 120 such as shown in FIG. 24 in a same manner as described in the first embodiment.

Next, the balloon catheter 2 is inserted into the bile duct via duodenal papilla, and the balloon 4 of the balloon catheter 2 is placed into the intrahepatic bile duct or a deeper portion of the common bile duct riding over the treatment target site (an inserting step S1). At this time, the fluid feeder 1201 and the balloon catheter 2 are not connected. Thus, no fluid is contained inside of the balloon 4, and the balloon is in a deflated state which is an original state of the balloon 4. Then, the user grips the grip 217 of the fluid feeder 1201, and the plunger main body 16 is moved to a direction in which it is pulled out from the cylinder 12 (called as a retraction movement). When the convex portion 14A disposed on the distal end of the adjustor 14 comes into contact to the fall-off prevention portion 19B disposed on the fixing portion 215 by the retraction movement of the plunger main body 16, the retraction movement of the plunger main body 16 relative to the cylinder 12 is regulated. At this state, the cylinder is filled with a fluid for inflating the balloon 4 to a specified maximum inflated diameter (for example, up to 20 mm in the present embodiment). Next, the user connects the cylinder 12 and the balloon catheter 2 (a connecting step S2).

In addition, an order of the inserting step S1 and the connecting step S2 described above are interchangeable. In this case, at first, the fluid feeder 1201 is connected to the first port 8 of the balloon catheter 2, then the balloon catheter 2 is inserted into the bile duct via duodenal papilla, and the balloon 4 of the balloon catheter 2 can be placed into the intrahepatic bile duct or a deeper portion of the common bile duct riding over the treatment target site.

Figure 25:
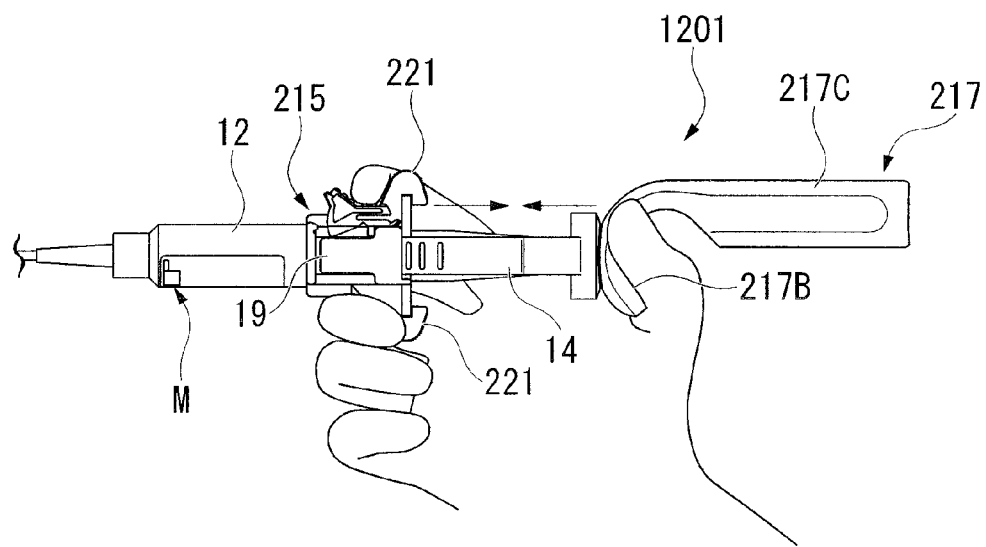
FIG. 25 shows an action of the fluid feeder supporting device during use.
Figure 26:
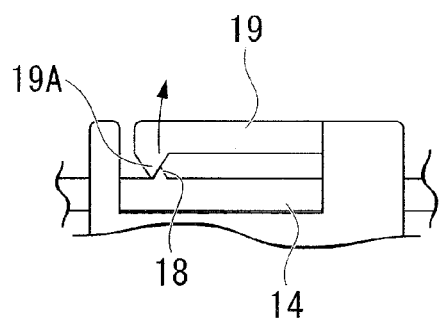
FIG. 26 shows an action of the fluid feeder supporting device during use.

Next, as shown in FIG. 25, the user places the thumb onto the index finger resting portion 217B and two of the remaining fingers are placed onto respective finger resting portions 221. In addition, although the present embodiment described that the fluid feeder 1201 is operated by one of the user's hands, the invention is not limited thereto. The fluid feeder 1201 can be operated by both of the user's hands such that the cylinder 12 or the fixing portion 215 may be held by one hand, and the grip 217 may be held by the other hand.

The user determines an inflating diameter of the balloon 4 according to a radiographic image showing a region including the patient's bile duct, and the user holds the finger resting portion 221 and the index finger resting portion 217B tighter so that these portions are made to come closer. As the result, the plunger main body 16 is inserted into the cylinder 12 so that the fluid filled inside of the cylinder flows into the balloon catheter 2 filling up the inside of the balloon 4 (a balloon inflating step S3).

In the balloon inflating step S3, the diameter of the balloon 4 may not have to be inflated to a specified diameter; for example, the diameter may be inflated to a standard diameter according to a different manipulation. The user can recognize an inflating size of the balloon 4 by feeling a number of a click which is caused when the engaging projections 18 of the adjustor 14 ride over the projection 19A of the engaged portion 19. In addition, the size of the inflating diameter of the balloon 4 can also be recognized from the marking M (referring to FIG. 25).

Figure 27:
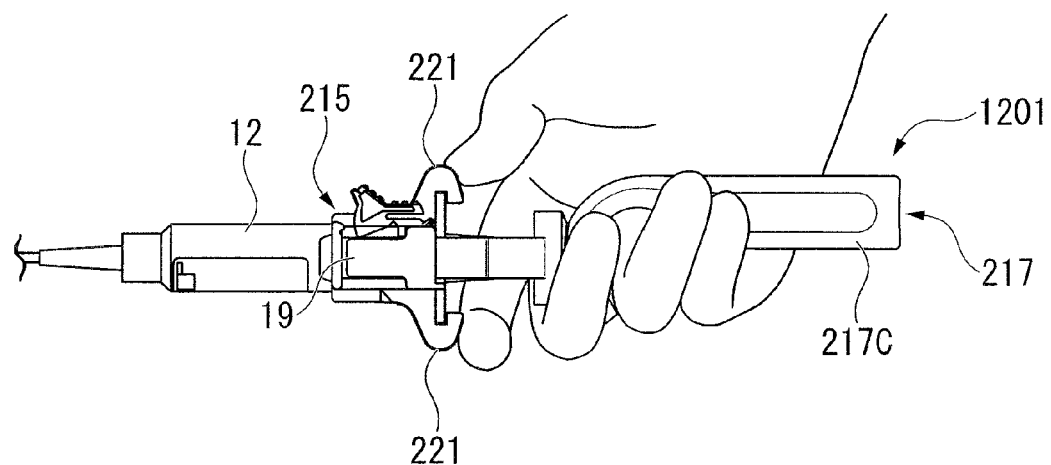
FIG. 27 shows an action of the fluid feeder supporting device during use.
Figure 28:
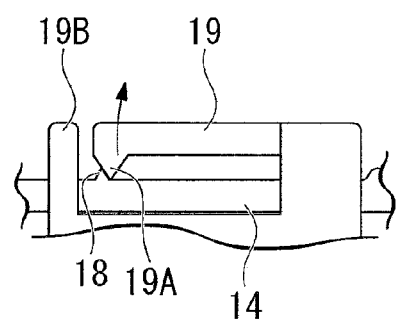
FIG. 28 shows an action of the fluid feeder supporting device during use.

Next, as shown in FIG. 27, the user places the thumb and the index finger on respective finger resting portions 221 and grips the grip 217 with the remaining fingers. At this time, the remaining fingers may grip other portions including the index finger resting portion 217B. Furthermore, by changing the position of the grip 217 around the axis thereof with respect to the user's hand, the user can grip the grip 217 at a suitable position for pulling and pushing the cylinder 12. For example, when the grip 217 is gripped with the middle, annular, little fingers; and the thumb and index fingers are placed on respective finger resting portions 221, the grip 217 may be positioned inside of the cylindrical shape formed with the middle, annular and little fingers are closed, opposing to a direction shown in FIG. 27. Then, the grip 217 may be gripped at a position in which the central axis O1 of the cylinder 12 aligns toward the thumb with respect to the central axis O2 of the grip 217.

Next, the user pulls and pushes the fixing portion 215 with respect to the grip 217 so that the plunger main body 16 is made to advance and retract with respect to the cylinder 12. Depending on the advanced or retracted distance between the adjacent engaging projections 18, the outer diameter of the balloon 4 is changed, and the diameter size is regulated to a suitable size to the manipulation (a balloon diameter regulating step S4, referring to FIGS. 26 and 28).

In the balloon diameter regulating step S4, the grip 217 may be gripped with at least one or more fingers from the middle, annular, little fingers, and the finger resting portions 221 may be supported by at least one or more fingers from the thumb and index fingers.

At this time, the balloon 4 is inflated so that a pressure which is a restoring force of the balloon 4 into a deflating status exerts onto the cylinder 12 from inside of the balloon 4. As described above, the projection 19A and the engaging projections 18 are constructed so that more force is required for the projection 19A to ride over the engaging projections 18 when the plunger main body 16 is retracted from the cylinder 12 toward the proximal end of the cylinder 12, and less force is required for the projection 19A to ride over the engaging projections 18 when the plunger main body 16 is advanced into the distal end of the cylinder 12. Hence, the movement of the projection 19A which unintentionally rides over the engaging projections 18 due the restoring force of the balloon 4 as described above is controlled.

Next, the balloon 4 is advanced into the duodenal papilla side by gradually withdrawing the balloon catheter 2 from the forceps port 121 according to the radiographic image showing a region including the patient's bile duct and the inflated balloon. At this time, the diameter of the balloon 4 is regulated with the same method as described in the balloon diameter regulating step S4, thereby the outer diameter of the balloon 4 can be fitted to the inner diameter of the bile duct and the like. Then, a treatment target such as a bile stone, biliary sludge or the like is discharged from the bile duct into the duodenum via duodenal papilla (a treating step S5).

The balloon catheter 2 is withdrawn from the forceps port 121, and the operation is continued with a different medical treatment, or completed by withdrawing the endoscope 120 from the patient's body cavity.

Further, similar to the fluid feeder 1 described in the first embodiment, the user may grip the grip 217 and place the fingers onto the finger resting portion 221, thereby the fluid feeder 1201 may be operated by pulling the cylinder 12 toward the grip 217 as shown in FIG. 8 in the balloon inflating step. In this case, the user can only change the position of the fingers on the finger resting portion 221 in the balloon inflating step, thereby it is not necessary to change the gripping position of the grip 217.

According to the fluid feeder 1201 and the fluid feeder supporting device 201 of the present embodiment, the cylinder 12 and the fixing portion 215 are detachably attached, and the cylinder 12 is prevented from falling off from the fluid feeder 1201 and the fluid feeder supporting device 201 by being fixed its position by the recessed portions 222, the projection 223 and the adjustor 14. Thereby, a step in which the cylinder 12 is fixed onto the fixing portion can be simplified.

Furthermore, the insertion of the wedged portion 220E into the space between the adjustor 14 and the engaged portion 19 can be realized by feeling a click, thereby the engagement between the engaging projections 18 and the projection 19A can be reliably released by opening the space between the adjustor 14 and the engaged portion 19 even when the wedged portion 220E can not be seen clearly such as being in the dark.

Also, since the fixing portion 215 and the switch 220 are integrally mounted and connected via the flexible hinge 220A, thereby the manufacturing and assembling the switch 220 can be simplified.

Moreover, since the sliding planes 19C, 19D supporting the adjustor 14 and the thread portion 19F are disposed on the engaged portion 19, thereby the adjustor 14 can be stably advanced and retracted along the longitudinal direction with respect to the engaged portion 19.

Furthermore, since the grip 217 having the index finger resting portion 217B is provided, the gripping position may be changed to an effective gripping position which suites for the different operations such that when the plunger main body 16 is inserted into the cylinder 12, and when the plunger main body 16 is pulled from the cylinder 12. In particular, with respect to the method of placing the thumb onto the index finger resting portion 217B, the fluid feeder 1201 can be operated with the same gripping position when a conventional syringe is gripped, thereby the user can operate the fluid feeder 1201 in a familiar manner.

Furthermore, the user can move the plunger main body 16 with respect to the cylinder 12 by one hand when the balloon 4 is inflated and deflated using the fluid feeder supporting device 201 and the fluid feeder 1201, thereby, the inflating and deflating operations can be easily performed. As a result, a diameter of the balloon can be easily adjusted to a desirable size by the user himself/herself, and even when the assistant helps the operation, working with the assistant is made easier.

Furthermore, since the rod member 217C of the grip 217 has a rod shape, the user can advance or retract the finger resting portion 221 with respect to the rod member 217C by one of or both of the thumb or index finger while griping the rod member 217C. At this time, a palm of the user acts as a fulcrum and one of or both of the user's thumb or index finger's ends act as a working point. Since the palm acts as the fulcrum, the advance and retracting movement of the plunger main body 16 with respect to the cylinder 12 by the user can be stably performed. Since the fixing portion 215 is also pushed by one of, or both of the thumb and the index finger with respect to the palm, a force to cause a fine advance and retraction movement can be easily controlled.

Furthermore, since the rod portion 217C extends along the axial line so that the user can grip at any position along the axis of the rod portion 217C, thereby the user can select a most preferable position for the manipulation with respect to the fixing portion 215.

Furthermore, the user can recognize the position of the index finger resting portion 217B by sense of touch while sliding their finger along the outer surface of the grip 217. Thus, the user can place the finger onto the index finger resting portion 217B without looking the portion or without taking the finger off from the grip 217 for searching a position for placing the finger. Thereby, the risk of dropping the fluid feeder 1202 and the fluid feeder supporting device 201 can be reduced, and gripping of fluid feeder 1202 and the fluid feeder supporting device 201 becomes unstable during the manipulation can be controlled.

(Forth Embodiment)

Next, a fluid feeder supporting device and a fluid feeder according to a forth embodiment of the present invention will be explained with reference to FIGS. 30A and 30B.

Similarly to the fluid feeder supporting device 201 of the third embodiment, the plunger main body 16 and the cylinder 12 are detachably disposed on the fluid feeder supporting device of the present embodiment, and it is used as a fluid feeder when the plunger main body 16 and the cylinder 12 are disposed thereon.

Figure 30A:
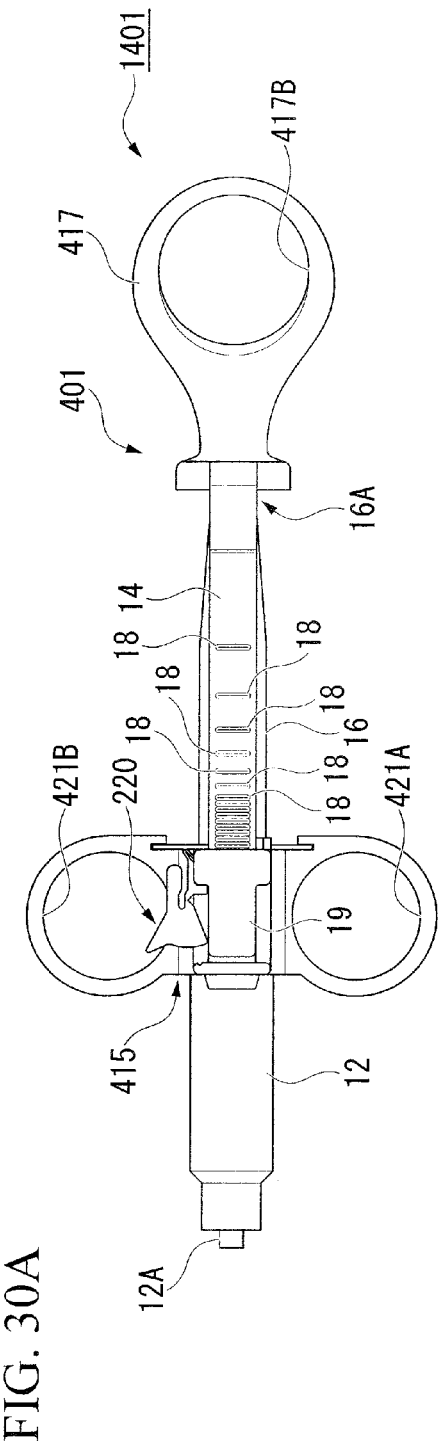
FIG. 30A is a perspective view showing the fluid feeder supporting device and the fluid feeder according to a forth embodiment of the present invention.
Figure 30B:
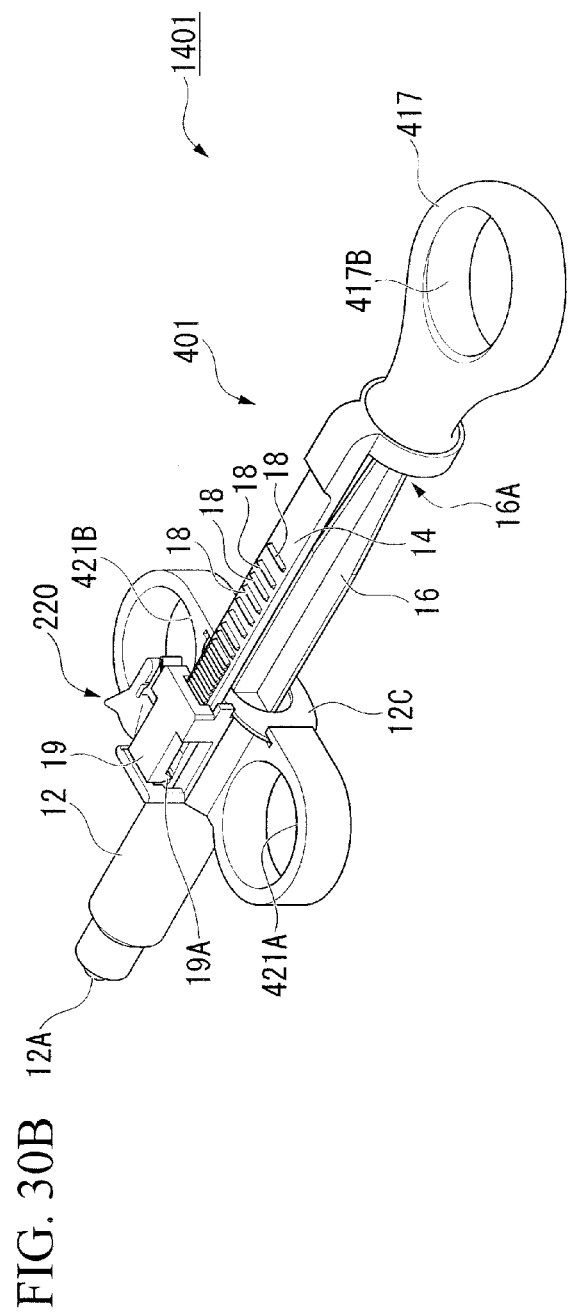
FIG. 30B is a front view of the fluid feeder supporting device and the fluid feeder.

FIG. 30A is a perspective view showing the fluid feeder supporting device 401 (hereinafter abbreviated as a fluid feeder 1401) after the main body 16 of the plunger and the cylinder 12 are disposed thereon. As shown in FIG. 30A, the fluid feeder 1401 includes a fixing portion 415 instead of the fixing portion 15, finger placing rings 421A, 421B instead of the finger resting portion 21, a grip 417 instead of the grip 17, and a index finger placing ring 417B is formed on the grip 417 instead of the index finger resting portion 217B.

The finger placing rings 421A, 421B are in a circular shape in which a finger of the user can be inserted through, and is formed on substantially the same plane. Furthermore, the finger placing rings 421A, 421B are fixed onto the fixing portion 415 or integrally mounted thereon. Similarly to the finger resting portion 221 in the third embodiment, it is also preferred that the finger placing rings 421A, 421B are placed in a off-set position to the engaged portion 19 side with respect to the central axis O2 of the cylinder 12. Each of the finger placing rings 421A, 421B may also oppose each other along at least on the axial line of the cylinder 12 or the plunger main body 16, and it is also acceptable if the ring shape of the finger placing rings 421A, 421B may not be continuous as long as a wall portion which supports the user's fingers is provided.

The index finger placing ring 417B is fixed to the adjustor 14 or is integrally mounted thereto, and is also detachably attached to the projected end 16A of the plunger main body 16 (referring to FIG. 21A). The index finger placing ring 417B is formed on substantially the same plane in which the finger placing rings 421A, 421B exist.

In the present embodiment, the user places the thumb onto the index finger placing ring 417B, and two of the remaining fingers are placed onto each of the finger placing rings 421A, 421B. By placing the fingers in this manner, the user can move the index finger placing ring 417B and the finger placing rings 421A, 421B closer to and away from the axial direction of the plunger main body 16.

Since the fluid feeder supporting device 401 is constructed such that the user places his/her fingers on the finger placing rings 421A, 421B and the index finger placing ring 417B so as to cause the advancing and retracting movements of the adjustor 14 and the fixing portion 415, the user does not need to change the holding direction of the fluid feeder 1401 even when the cylinder 12 and the plunger main body 16 are moved to a different direction along the axial line relative to each other.

Also, since the shape of the finger placing rings 421A, 421B disposed on the fixing portion 415 and the index finger placing ring 417B disposed on the adjustor 14 are in a similar shape to a ring-shaped finger placing portion of a conventional syringe adaptor, a user who has experience using the conventional syringe adaptor will recognize which fingers should be placed onto which of the finger placing rings even if seeing the finger placing rings 421A, 421B and the index finger placing ring 417B at a first time. Thereby, an operation failure due to erroneous use of the fluid feeder 1401 can be prevented.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

For example, as shown in FIGS. 10 and 13, in the proceeding embodiment, the angle of slant faces of both distal and proximal sides of the engaging projections of the adjustor were the same. However, the shape of the engaging projections is not limited thereto. Modified examples are described herein below.

Figure 14:
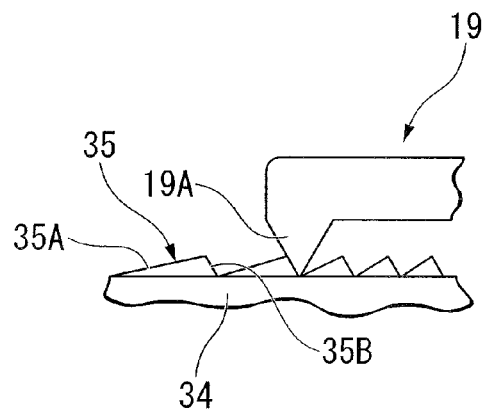
FIG. 14 is an enlarged view of the adjustor and the engaged portion of a fluid feeder according to a modified examples of the present invention.

FIG. 14 is an enlarged view of an adjustor 34 as a modified example of the present invention. An angle formed by a first slant face 35A (at a distal side) between a base of the adjustor 34 parallel to an axis of the plunger 13 (in other words, it is an angle formed by the first slant face 35A between the axis of the plunger 13) is set smaller than that of a second slant face 35B (at the proximal side). As a result of this design, lesser force is required for the projection 19A to ride over the engaging projections 35 when the plunger 13 is advanced. Therefore, the inflation operation of the balloon 4 can be easily performed as well as having an advantage of reliably controlling the diameter of the balloon.

Figure 15:
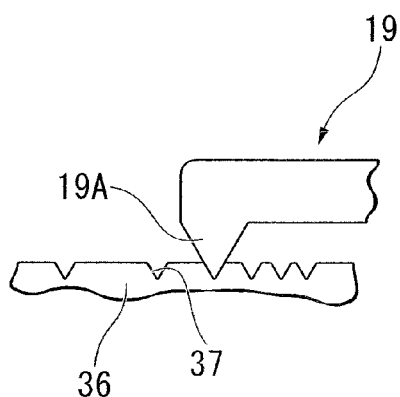
FIG. 15 is an enlarged view of the adjustor and the engaged portion of a fluid feeder according to a modified examples of the present invention.
Figure 16A:
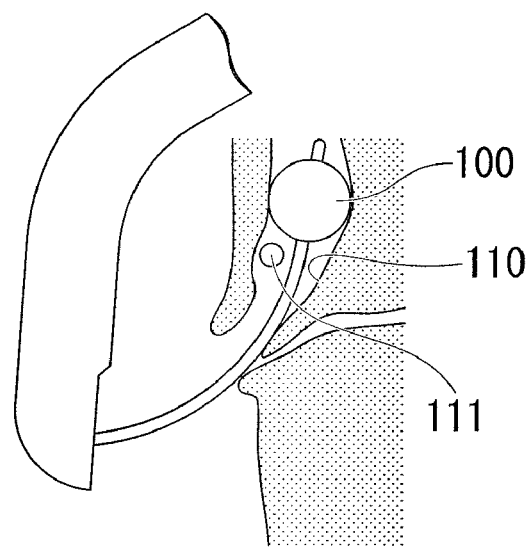
FIG. 16A shows a state in which a gallstone is removed by a conventional balloon catheter.
Figure 16B:
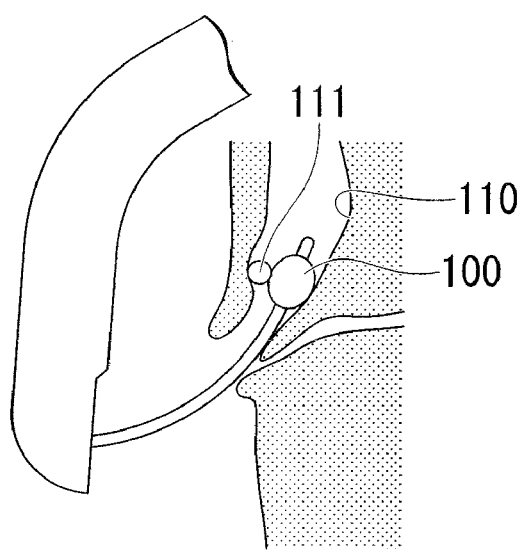
FIG. 16B shows a state in which a gallstone is left in the vicinity of an entry of a bile duct.

Alternatively, in the proceeding embodiment, the projection of the engaged portion and the engaging projections of an adjustor were engaged. However, in place thereof, it is also acceptable to design a concave portion 37 on an adjustor 36 which engages with the projection 19A of the engaged portion 19 as shown in a modified example of FIG. 15. In this case, in order to increase the engagement force at the concave portion 37 as the moving distance of the plunger 13 increases, a depth of the concave portion 37 may be increased as the position is closer to the proximal end of the adjustor 36.

Further, a fixing portion may be constructed by providing the concave portion at the engaged portion so as to engage with the engaging projections of the adjustor; or different angles may be formed at the first slant face and the second slant face between the axis of the plunger, as shown in the aforementioned modified example.

For example, the proceeding embodiments described examples in which a fluid feeder was used in the balloon catheter. However, the invention is not limited thereto; for example, the fluid feeder of the present invention may also be used in, for example, an inner diameter measuring device which measures an inner diameter of the tube by inflating a balloon in the tube so as to fit into. The inner diameter can be measured easily since the diameter of the balloon can be regulated at a desirable size.

Finally, the invention is not to be considered as being limited by the foregoing description and is only limited by the scope of the appended claims.

What is claimed is:

1. A fluid feeder which feeds a fluid into a balloon made of an elastic material so as to inflate, the fluid feeder comprising:
    a cylinder that is formed in a cylindrical shape provided with a first end of a distal end side and a second end of a proximal end side and contains the fluid,
    a plunger that is inserted into the cylinder via the second end in a freely advancing and retracting manner in an axial direction, in order to push out the fluid contained in the cylinder from the first end to the outside of the cylinder,
    a plurality of engaging members to regulate the moving distance of the plunger so as to set a predetermined distance, and
    an engaged portion provided on the cylinder, which fixes the plunger to a position that corresponds to the predetermined distance regulated by engaging with the engaging members, wherein the plurality of engaging members comprises:
        a first engaging member disposed along a moving direction of the plunger;
        a second engaging member located closest to a proximal side of the plunger than the first engaging member, member and the second engaging member disposed in a linear arrangement, wherein the second engaging member is the next closest to the first engaging member in the proximal direction; and
        a third engaging member located closer to a proximal side of the plunger than the second engaging member, the first engaging member, second engaging member and third engaging member disposed in a linear arrangement, wherein the third engaging member is the next closest to the second engaging member in the proximal direction, and, wherein
        a distance between the second engaging member and the third engaging member is longer than a distance between the first engaging member and the second engaging member so that the moving distance of the plunger is capable of varying with respect to a movement of the plunger.

2. The fluid feeder according to claim 1, wherein the series of the plurality of the engaging members is constructed so as to change an inflated diameter of the balloon by a predetermined amount.

3. The fluid feeder according to claim 1, wherein the series of the plurality of the engaging members is constructed so as to increase an engagement force exerted between the engaging members and the cylinder as the inflated diameter of the balloon increases.

4. The fluid feeder according to claim 1, wherein each of the engaging members has a first slant face at a distal side which is inserted into the cylinder and a second slant face at a proximal side along an axial direction of the plunger, an angle formed by the first slant face between the axis of the plunger is smaller than an angle formed by the second slant face between the axis of the plunger.

5. A balloon catheter made of an elastic material provides with the fluid feeder according to claim 1.

6. The fluid feeder according to claim 1, wherein
    the engaging members and the engaged portion can relatively advance and retract along the axis of the cylinder;
    a first end of the engaged portion is fixed to the cylinder and a second end is formed like a plate spring extending to a direction in which a main body of the plunger is inserted into the cylinder; and
    a projection is formed on the second end so as to abut the engaging members.

7. The fluid feeder according to claim 6, wherein the plate spring configuring the second end of the engaged portion is configured to have a biasing force toward a direction where the plate spring exerts a fixing force against at least one of the engaging members.

8. The fluid feeder according to claim 1, wherein the plunger is provided with a finger resting portion used for a main body of the plunger to be compressed and is moved to a direction in which the plunger is inserted into the cylinder.

9. A method of feeding a fluid using the fluid feeder according to claim 8, comprising:
    inflating the balloon inside of a hollow organ by manipulating the fluid feeder or the fluid feeder supporting device such that a thumb is placed on a finger resting portion disposed on the plunger and one or more fingers from the remaining fingers are placed on a portion of the cylinder: and
    placing the thumb and an index finger on a portion of the cylinder for supporting the cylinder while gripping the plunger by placing one or more fingers from a middle, an annular and a little finger so as to cause the cylinder and the plunger to move relatively along the axial direction; and
    inflating the balloon or adjusting the inflated diameter.

10. A medical treatment method for treating a treatment target on a lumen of a hollow organ using the fluid feeder according to claim 8, comprising:

inserting a balloon catheter provided with an elastic balloon into the hollow organ and guiding the balloon catheter to a treatment target;

connecting the fluid feeder or the fluid feeder supporting device to the balloon catheter;

inflating the balloon inside of the hollow organ by manipulating the fluid feeder or the fluid feeder supporting device such that a thumb is placed on a finger resting portion disposed on the plunger and one or more fingers from the remaining fingers are placed on a portion of the cylinder;

placing the thumb and an index finger on a portion of the cylinder for supporting the cylinder while gripping the plunger by placing one or more fingers from a middle, an annular and a little finger so as to cause the cylinder and the plunger to move relatively along the axial direction;

inflating the balloon or adjusting the inflated diameter; and performing a medical treatment to the treatment target by the balloon.

11. The fluid feeder according to claim 1 further provided with a switch connected via a flexible hinge on the cylinder, wherein the switch is provided with a hook which fixes a switch proximal end portion adjacent to the hinge, a switch distal end portion which freely oscillates with respect to the switch proximal end portion, and a wedged portion is formed on the switch distal end portion, that is inserted between the plunger and the engaged portion so as to open a space between the plunger and the engaged portion, and an engagement between the engaging members and the engaged portion is released; and the cylinder, the hinge and the switch are integrally mounted.

12. The fluid feeder according to claim 11, wherein the switch and the cylinder are integrally molded via the flexible hinge.

13. The fluid feeder according to claim 1, wherein the plunger is provided with a grip which can be gripped and is used for making the plunger advance and retract with respect to the cylinder.

14. A fluid feeder supporting device detachably attached to a cylinder and a plunger main body which is used for supplying a fluid into a balloon made of an elastic material so as to inflate, the fluid feeder supporting device comprising:

an adjustor that is detachably attached to the plunger main body and regulates a moving distance of the plunger main body so as to inflate the balloon to a predetermined diameter the adjuster having a plurality of engaging members provide with the adjuster in order to regulate the moving distance of the plunger so as to set a predetermined distance, and a fixing portion that is detachably attached on the cylinder and fixes the plunger onto the cylinder to a position which corresponds to the moving distance regulated by the adjustor, the fixing portion having an engaged portion provided on the fixing portion that fixes the plunger to a position that corresponds to the predetermined distance regulated by engaging with the engaging members, wherein the plurality of engaging members comprises:

a first engaging member disposed along a moving direction of the plunger;

a second engaging member located closer to a proximal side of the plunger than the first engaging member, member and the second engaging member disposed in a linear arrangement, wherein the second engaging member is the next closest to the first engaging member in the proximal direction; and a third engaging member located closer to a proximal side of the plunger than the second engaging member, the first engaging member, second engaging member and third engaging member disposed in a linear arrangement, wherein the third engaging member is the next closest to the second engaging member in the proximal direction, and, wherein a distance between the second engaging member and the third engaging member is longer than a distance between the first engaging member and the second engaging member so that the moving distance of the plunger is capable of varying with respect to a movement of the plunger.

15. The fluid feeder according to claim 1 or the fluid feeder supporting device according to claim 14, further comprising a grip, wherein the grip and the plunger are detachably attached.

16. The fluid feeder according to claim 1 or the fluid feeder supporting device according to claim 14, further comprising a grip, wherein the grip is formed on the plunger extending to an axial direction of the plunger.

17. The fluid feeder according to claim 1 or the fluid feeder supporting device according to claim 14, wherein the grip is in a rod shape.

18. The fluid feeder according to claim 1 or the fluid feeder supporting device according to claim 14, further comprising a grip, wherein the grip is in a off-set position to a radial direction of the plunger with respect to the axis of the plunger.

19. A method of feeding a fluid using the fluid feeder according to claim 1 comprising:

placing a thumb and an index finger on a portion of the cylinder for supporting the cylinder while gripping the plunger by placing one or more fingers from a middle, an annular and a little finger so as to cause the cylinder and the plunger to move relatively along the axial direction; and inflating the balloon or adjusting the inflated diameter.

20. A medical treatment method for treating a treatment target on a lumen of a hollow organ using the fluid feeder according to claim 1, comprising:

inserting a balloon catheter provided with an elastic balloon into the hollow organ and guiding the balloon catheter to a treatment target;

connecting the fluid feeder or the fluid feeder supporting device to the balloon catheter;

inflating the balloon inside of the hollow organ;

inflating the balloon or regulating the balloon diameter by moving the cylinder and the plunger along the axial direction relative to engaging members depending on a distance between each of the adjacent engaging members; and performing a medical treatment to the treatment target by the balloon.

21. A medical treatment method according to claim 20, wherein placing at least one of a thumb and an index finger on a portion of the cylinder for supporting the cylinder while gripping the plunger by placing one or more fingers from a middle, an annular and a little finger so as to cause the cylinder and the plunger to move relatively along the axial direction; and inflating the balloon.

22. The fluid feeder according to claim 1 or the fluid feeder supporting device according to claim 14, wherein the series of the plurality of the engaging members have a first slant face at a distal side which is inserted into the cylinder and a second slant face at the proximal side along an axial direction of the plunger, an angle formed by the first slant face between the axis of the plunger is the same as an angle formed by the second slant face between the axis of the plunger,
  wherein the engaging members are constructed so as to increase a space between the adjacent engaging member and to increase a size of each of the engaging member as the inflated diameter of the balloon increases.

23. The fluid feeder according to claim 1, wherein a distance between the plurality of engaging members are configured so that the moving distance of the plunger becomes large in accordance with an increase of a supplied amount of the fluid to the balloon, such that an amount of change of the outer diameter of the balloon in accordance with the movement of the plunger to an adjacent engaging member becomes constant.

24. The fluid feeder according to claim 1, wherein the balloon is a single balloon.

25. The fluid feeder according to claim 1 or the fluid feeder supporting device according to claim 14, further comprising a grip, wherein
  the grip is disposed on an end of the plunger at a position projected from the cylinder.

26. The fluid feeder supporting device according to claim 14, wherein the series of the plurality of the engaging members is constructed so as to change an inflated diameter of the balloon by a predetermined amount.

27. The fluid feeder supporting device according to claim 14, wherein the series of the plurality of the engaging members is constructed so as to increase an engagement force exerted between the engaging members and the engaged portion as the inflated diameter of the balloon increases.

28. The fluid feeder supporting device according to claim 14, wherein each of the engaging members has a first slant face at a distal side which is inserted into the cylinder and a second slant face at a proximal side along an axial direction of the plunger, an angle formed by the first slant face between the axis of the plunger is smaller than an angle formed by the second slant face between the axis of the plunger.

29. A balloon catheter provided with a balloon made of an elastic material, that is provides with the fluid feeder supporting device according to claims 14.

30. The fluid feeder supporting device according to claim 14, wherein the engaging members and the engaged portion can be relatively advanced and retracted along the axis of the cylinder;
  a first end of the engaged portion is fixed to the cylinder and a second end is formed like a plate spring extending to a direction in which the plunger main body is inserted into the cylinder; and
  a projection is formed on the second end so as to abut the engaging members.

31. The fluid feeder supporting device according to claim 14, wherein the plunger is provided with a finger resting portion used for the plunger main body to be compressed and is moved to a direction in which the plunger is inserted into the cylinder.

32. The fluid feeder supporting device according to claim 14 further provided with a switch connected via a flexible hinge on the cylinder,
  wherein the switch is provided with a hook which fixes a switch proximal end portion adjacent to the hinge,
  a switch distal end portion which freely oscillates with respect to the switch proximal end portion, and
  a wedged portion is formed on the switch distal end portion, that is inserted between the plunger and the engaged portion so as to open a space between the plunger and the engaged portion, and an engagement between the engaging members and the engaged portion is released; and
  the cylinder, the hinge and the switch are integrally mounted.

* * * * *